(12) United States Patent
Rogan

(10) Patent No.: US 7,811,766 B2
(45) Date of Patent: Oct. 12, 2010

(54) **GENETIC IDENTIFICATION AND VALIDATION OF *ECHINACEA* SPECIES**

(75) Inventor: Peter K. Rogan, Leawood, KS (US)

(73) Assignee: ThinkVillage, LLC, Boulder, CO (US)

( * ) Notice: Subject to any disclaimer, the term of this patent is extended or adjusted under 35 U.S.C. 154(b) by 100 days.

(21) Appl. No.: 12/058,353

(22) Filed: Mar. 28, 2008

(65) Prior Publication Data

US 2009/0081657 A1 Mar. 26, 2009

Related U.S. Application Data

(60) Provisional application No. 60/908,586, filed on Mar. 28, 2007.

(51) Int. Cl.
*C12Q 1/68* (2006.01)
*C12P 19/34* (2006.01)
*C07H 21/04* (2006.01)

(52) U.S. Cl. .......................... 435/6; 435/91.2; 536/23.1; 536/24.33

(58) Field of Classification Search .................. 435/6, 435/91.2; 536/23.1, 24.33
See application file for complete search history.

(56) References Cited

U.S. PATENT DOCUMENTS

| | | | |
|---|---|---|---|
| 5,426,027 A * | 6/1995 | Lott et al. ..................... 435/6 |
| 5,547,835 A | 8/1996 | Koster |
| 5,622,824 A | 4/1997 | Koster |
| 5,691,141 A | 11/1997 | Koster |
| 5,849,492 A | 12/1998 | Rogan |
| 5,851,765 A | 12/1998 | Koster |
| 5,872,003 A | 2/1999 | Koster |
| 6,074,823 A | 6/2000 | Koster |
| 6,140,053 A | 10/2000 | Koster |
| 6,194,144 B1 | 2/2001 | Koster |
| 6,225,450 B1 | 5/2001 | Koster |
| 6,238,871 B1 | 5/2001 | Koster |
| 6,268,131 B1 | 7/2001 | Kang et al. |
| 7,108,974 B2 | 9/2006 | Ecker et al. |
| 7,217,510 B2 | 5/2007 | Ecker et al. |
| 7,226,739 B2 | 6/2007 | Ecker et al. |
| 7,255,992 B2 | 8/2007 | Ecker et al. |
| 2004/0161770 A1 | 8/2004 | Ecker et al. |
| 2004/0209260 A1 | 10/2004 | Ecker et al. |
| 2004/0219517 A1 | 11/2004 | Ecker et al. |
| 2005/0130196 A1 | 6/2005 | Hofstadler |
| 2005/0164215 A1 | 7/2005 | Hofstadler |
| 2005/0266397 A1 | 12/2005 | Ecker et al. |
| 2005/0270191 A1 | 12/2005 | Hofstadler |
| 2006/0121520 A1 | 6/2006 | Ecker et al. |
| 2006/0205040 A1 | 9/2006 | Sampath et al. |
| 2006/0240412 A1 | 10/2006 | Hall |
| 2006/0259249 A1 | 11/2006 | Sampath et al. |
| 2006/0275749 A1 | 12/2006 | Sampath et al. |
| 2006/0275788 A1 | 12/2006 | Ecker et al. |
| 2007/0264639 A1 * | 11/2007 | Zenser et al. .................. 435/6 |

OTHER PUBLICATIONS

The search reports. Baldwin et al. Systematic botany, 2002, vol. 27(1). p. 161-198.*
Schilling et al. Botanical Journal of the Linnean Society, 2002, vol. 140, p. 65-76.*
Lowe et al. Nucleic acid research, 1990, vol. 18(7).*
Aceto, S., et al.; Phylogeny and evolution of Orchis and allied genera based on ITS DNA variation: morphological gaps and molecular continuity; Mol Phylogenet Evol., Oct. 1999;13(1); pp. 67-76.
Ainouche, M.L. & Bayer, R.J. "On the origins of the tetraploid *Bromus* species (section *Bromus*, Poaceae): insights from internal transcribed spacer sequences of nuclear ribosomal DNA" Genome, Oct. 1997; 40(5); pp. 730-743.
Bains, W. "DNA Sequencing by Mass Spectrometry. Outline of a Potential Future Application" Chimicaoggi. vol. 9, No. 10, Oct. 1991; pp. 13-16, 1991.
Binns, S.E., et al "A taxonomic revision of *Echinacea* (Asteraceae: Heliantheae)" Syst. Bot. 2002, vol. 27, pp. 610-632.
Bobowski, B.R., et al. "Identification of roots of woody species using polymerase chain reaction (PCR) and restriction fragment length polymorphism (RFLP) analysis" Mol Ecol. Mar. 1999; 8(3); pp. 485-491.
Chen, C.H. Winston, et al.; Laser Desorption Mass Spectrometry for Fast DNA Sequencing; U.S. Department of Energy, DOE Human Genome Program Contractor-Grantee Workshop IV, 1994; retrieved from http://www.ornl.gov/sci/techresources/Human—Genome/publicat/94SANTA/sequencing/chen.shtml.
Chen, C.H. Winston, et al.; Laser Desorption Mass Spectrometry for DNA Sequencing and Analysis; Session K14—Nucleic Acids; MIXED session, Tuesday afternoon, Mar. 17, 1998, Los Angeles Convention Center; retreived from http://flux.aps.org/meetings/YR98/BAPSMAR98/abs/S2000012.html.
Chen, C.H., et al.; Laser Desorption Mass Spectrometry for high throughput DNA analysis and its applications; 1999; retrieved from http://www.osti.gov/bridge/servlets/purl/3655-nx94bv/webviewable/3655.pdf.
Chen, C.H. Winston, et al.; Laser Desorption Mass Spectrometry for DNA Sequencing and Analysis; DOE Human Genome Program Contractor-Grentee Workshop VIII Jan. 12-16, 1999 Oakland, CA; retrieved from http://www.ornl.gov/sci/techresources/Human—Genome/publicat/99santa/45.html.
Chen, C.H. Winston, et al.; Laser mass sepctrometry for DNA sequencing, disease diagnosis, and fingerprinting; SPIE vol. 2985; 1997; pp. 70-81.

(Continued)

*Primary Examiner*—Kenneth R. Horlick
*Assistant Examiner*—Joyce Tung
(74) *Attorney, Agent, or Firm*—Lathrop & Gage LLP

(57) ABSTRACT

A method for identification and validation of *Echinacea* is disclosed. Primers are designed based on information analysis of sequences from a large number of *Echinacea* species to amplify certain segments of genomic DNA to identify the species. Primers and methods are also disclosed to amplify other plant species that are frequently found in adulterated herbal samples of *Echinacea*.

14 Claims, 15 Drawing Sheets

OTHER PUBLICATIONS

Emshwiller, E. & Doyle, J.J.; Origins of domestication and polyploidy in oca (*Oxalis tuberosa*:Oxalidaceae). 2. Chloroplast expressed glutamine synthetase data. American Journal of Botany 89(7), 2002; pp. 1042-1056.

Emshwiller, E. & Doyle, J.J; Origins of domestication and polyploidy in oca (*Oxalis tuberosa*:Oxalidaceae): nrDNA ITS data. American Journal of Botany 85(7); 1998; pp. 975-985.

Ecker, D.J., et al. "Rapid identification and strain-typing of respiratory pathogens for epidemic surveillance" Proc Natl Acad Sci USA 102(22); May 2005, pp. 8012-8017.

Ecker, D.J., et al. "The Microbial Rosetta Stone Database: a compilation of global and emerging infectious microorganisms and bioterrorist threat agents" BMC Microbio15(1):19, (2005); 17 pages.

Ecker, J.A., et al. "Identification of *Acinetobacter* species and genotyping of *Acinetobacter baumannii* by multilocus PCR and mass spectrometry" J Clin Microbio144(8), (2006), pp. 2921-2932.

Edwards, J.R., et al; Mass-Spectrometry DNA Sequencing; Mutation Research 573 (2005) 3-12.

Edwards, J.R. et al.; DNA sequencing using biotinylated dideoxynucleotides and mass spectrometry; Nucleic Acids Research 2001, vol. 69, No. 21, e104; pp. 1-6.

Fitzgerald, M.C. et al; The Analysis of Mock DNA Sequencing Reactions Using Matrix-assisted Laser Desporption/Ionization Mass Spectrometry; Rapid Communications in Mass Spectrometry, vol. 7; 895-897 (1993).

Francisco-Ortega J., et al., Internal Transcribed Spacer Sequence Phylogeny of *Crambe* L. (Brassicaceae): Molecular Data Reveal Two Old World Disjunctions; Mol Phylogenet Evol., Apr. 1999; 11(3); pp. 361-380.

Hall, T.A. et al.; Base composition analysis of human mitochondrial DNA using electrospray ionization mass spectrometry: a novel tool for the identification and differentiation of humans; Analytical Biochem. 344 (2005); pp. 53-69.

Herwig, R., et al.; Information theoretical probe selection for hybridisation experiments; vol. 16, No. 10, 2000, pp. 890-898.

Hujer, K.M. et al. "Analysis of antibiotic resistance genes in multidrug-resistant *Acinetobacter* sp. isolates from military and civilian patients treated at the WalterReed Army Medical Center" Antimicrob Agents Chemother 50(12), (2006), pp. 114-123.

Jacobson, K.B. et al.; Applications of mass spectrometry to DNA sequencing; GATA 8(8), 1991; pp. 223-229.

Jupe, E.R. & Zimmer, E.A.; Unmethylated regions in the intergenic spacer of maize and teosinte ribosomol RNA genes; Plant Mol Biol.; Mar. 1990;14(3); pp. 333-347.

Kirpekar, F., et al.; DNA sequence analysis my MALDI mass spectrometry; Nucleic Acids Research, 1998, vol. 26, No. 11; pp. 2554-2559.

Kim, D.H. et al.; Genetic diversity of *Echinacea* species based upon amplified fragment length polymorphism markers. Genome, Feb. 2004; 47(1); pp. 102-111.

Koopman, W.J.M., et al., Phylogenetic Relationships Among *Lactuca* (Asteraceae) Species and Related Genera Based on ITS-1 DNA Sequences; Am. J. Bot. 85(11), 1998; pp. 1517-1530.

Koster, H. et al.; A strategy for rapid and efficient DNA sequencing by mass spectrometry; Nature Biotech; vol. 14, Sep. 1996; pp. 1123-1128.

Krause, J. et al.; High Resolution Characterization of DNA Fragment Ions Produced by Ultraviolet Matrix-Assisted Laser Desporption/Ionization Using Linear and Reflecting Time-of-Flight Mass Spectrometry; J. Am. Soc. Mass Spectrom., 1999, 10, pp. 423-429.

Lesnik et al. (2005) "Identification of conserved regulatory RNA structures in prokaryotic metabolic pathway genes" Biosystems 80(2):145-54.

Little, D.P., et al.; Rapid Sequencing of Oligonucleotides by High-Resolution Mass Spectrometry; J. Am Chem Soc. 116, 1994, pp. 4893-4897.

Little, D.P. & McLafferty, F.W.; Sequencing 50-mer DNAs Using Electrospray Tandem Mass Spectrometry and Complementary Fragmentation Methods; J. Am Chem Soc. 117, 1995, pp. 6783-6784.

Little, D.P., et al.; Sequencing Information from 42—108-mer DNAs (Complete for a 50-mer) by Tandem Mass Spectrometry; J. Am Chem Soc. 118, 1996, pp. 9352-9359.

Little, D.P., et al.; Verification of 50- 100-mer DNA and RNA sequences with high resolution mass spectrometry; Proc. Natl. Acad. Sci. USA vol. 92, Mar. 1995, pp. 2318-2322.

Liu, J.-S. & Schardl, C.L.; A conserved sequence in internal transcribed spacer 1 of plant nuclear rRNA genes; Plant Mol Biol., Oct. 1994 vol. 26, No. 2, pp. 775-778.

Martin, W.J.; New technologies for large-genome sequencing; Genome vol. 31, 1989; pp. 1073-1080.

Murray, K.K.; Special Feature: Tutorial—DNA Sequencing by Mass Spectrometry; Journal of Mass Spectrometry; vol. 31, 1996; pp. 1203-1215.

Nelson, R.W., et al.; Volitization of High Molecular Weight DNA by Pulsed Laser Ablation of Frozen Aqueous Solutions; Science vol. 246; Dec. 1989; pp. 1585-1587.

Ni, J. et al.; "Interpretation of Oligonucleotide Mass Spectra for Determination of Sequence Using Electrospray Ionization and Tandem Mass Spectrometry"; Anal. Chem 1996, vol. 68, No. 13; pp. 1989-1999.

Nordhoff, E. et al.; Direct Mass Spectrometric Sequencing of Low-picomole Amounts of Oligodeoxynucleotides with up to 21 Bases by Matrix-assisted Laser Desorption/Ionization Mass Spectrometry; Journal of Mass Spectrometry; vol. 30 (1995); pp. 99-112.

Parr, G.R., et al; "Matrix-Assisted Laser Desorption/Ionization Mass Spectrometry of Synthetic Oligodeoxyribonucleotides", Rapid Communications in Mass Spectrometry, 1992, 6, 369-372.

Reamon-Buttner, S.M., et al., AFLPs represent highly repetitive sequences in *Asparagus officinalis* L. C. Chromosome Res.; 1999, vol. 7 No. 4; pp. 297-304.

Rogan P.K., et al.;Visual Display of Sequence Conservation as an Aid to Taxonomic Classification Using PCR Amplification; In: Visualizing Biological Information, CA Pickover (ed). World Scientific, River Edge NJ, 1995; pp. 21-32.

Roskey, M.T., et al.; DNA sequencing by delayed extraction-matrix-assisted laser desporption/ionization time of flight mass spectrometry; Proc Natl. Acad. Sci. USA, vol. 93, May 1996, pp. 4724-4729.

Sakai, R.K., et al.; Enzymatic amplification of beta-globin genomic sequences and restriction site analysis for diagnosis of sickle cell anemia; Science 20; Dec. 1985; pp. 1350-1354.

Sampath, R. et al. (2005) Rapid identification of emerging Infectious agents Using PCR and Electrospray Ionization Mass Spectrometry; Ann. N.Y. Acad. Sci. 1102 (2007); pp. 109-120.

Sampath, R. et al. "Rapid identification of emerging pathogens: coronavirus" Emerg Infect Dis (2005) 11(3): 373-9.

Sanger F, et al. "DNA sequencing with chain-terminating inhibitors." Proc Natl Acad Sci U S A. 1977 74 (12); pp. 5463-5467.

Schneider, T.D. & Stephens, R.M.; Sequence logos: a new way to display consensus sequences; Nucleic Acids Research; vol. 18, No. 20, 1990, pp. 6097-6100.

Schneider, T.D., et al.; Information Content of Binding Sites on Nucleotide Sequences; J. Mol. Biol. (1986) 188; pp. 415-431.

Seth, P.P.; et al; Discovery of a New Class of RNA-Binding Small Molecules for the Hepatitis C Virus: Internal Ribosome Entry Site IIA Subdomain; J. Med. Chem. 48 (2005); pp. 7099-7102.

Siudzak, G. "The emergence of mass spectrometry in biochemical research" Proc. Natl Acad Sci USA, vol. 91, Nov. 1994, pp. 11290-11297.

Skinner, K.A.; Bacterial contaminants of fuel ethanol production; J. Ind. Microbiol. Biotechnol. vol. 31, 2004; pp. 401-408.

Soltis, P.S. & Soltis, D.E.; The role of genetic and genomic attributes in the success of polyploids Proc Natl Acad Sci USA, Jun. 2000; 97(13); pp. 7051-7057.

Stimpel, M., et al.; Macrophage Acivation and Induction of Macrophage Cytotoxicity by Purified Polysaccharide Fractions from the Plant *Echinecea purpurea*; Infection and Immunity, vol. 46, No. 3, Dec. 1984; pp. 845-849.

Tang, K., et al., Mass-Spectrometry of Laser-Desorbed Oligonucleotides. Rapid Communications in Mass Spectrometry, 1992. 6(6): p. 365-368.

Tang, W., et al.; Controlling DNA Fragmentation in MALDI-MS by Chemical Modification; Anal. Chem., vol. 69, 1997, pp. 302-312.

Tang K, et al.; Matrix-assisted laser desorption/ionization mass spectrometry of immobilized duplex DNA probes. Nucleic Acids Res. Aug. 25, 1995; 23(16); pp. 3126-3131.

Tooley, P.W., et al.; Phylogenetic Inference Based on Information Theory-Based PCR Amplification; J. Phytopathology, vol. 146; (1998) pp. 427-430.

Van Der Stappen, J., et al.; Sequencing of the Internal transcribed spacer region ITS1 as a molecular tool detecting variation in the *Stylosanthes gulanenis* species complex; Theor. Appl. Genet. 96, 1998, pp. 869-877.

Van Ert et al. (2004) "Mass spectrometry provides accurate characterization of two genetic marker types in *Bacillus anthracis*" Biotechnigues 37(4):642-4.

Whiting, M., et al.; Detection of *pediococcus* spp. in Brewing Yeast by a Rapid Immunoassy; Appl. Environ. Microbiol., vol. 58, No. 2, Feb. 1992; pp. 713-716.

Woese, C.R.; Bacterial Evolution; Microbiol Rev. Jun. 1987 51(2); pp. 221-271.

Wu, K.J., et al.; Time-of-Flight Mass Spectrometry of Underivatized Single-Stranded DNA Oligomers by Matrix-Assisted Laser Desorption, Anal. Chem., 1994, pp. 1637-1645.

Maxam, A.M. & Gilbert, W., "Sequencing end-labeled DNA with base-specific chemical cleavages." Methods Enzymol.; ed. Grossman & Moldave; 1980 vol. 65(1):499-560.

* cited by examiner

```
                        1                                                50
    E.paradoxa   tcgaatcctg catagcagaa cgacccgtga acatgtaaaa actact.ggc    SEQ ID No. 1
    E.simulata   tcgaatcctg catagcagaa cgacccgtga acatgtataa actact.ggc    SEQ ID No. 2
     E.pallida   tcgaatcctg catagcagaa cgacccgtga acatgtaaaa actact.ggc    SEQ ID No. 3
    E.purpurea   tcgaatcctg catagcataa cgacccgtga acatgtaaaa actactggcc    SEQ ID No. 4
 E.tenesseensi   tcgaatcctg .atagcagaa cgacccgtga acatgtaaaa actacttggt    SEQ ID No. 5
   E.atrorubens  tcgaaccctg catagcagaa cgacccgtga acatgtaaaa a.tactggcc    SEQ ID No. 6

51                                               100
                 ctttcgggga ccgaagcatt tgtttcgagc cttgtgaggc cttgttgacg
                 ctttcgggga ccgaagcatt tgtttcgagc cttgtgaggc cttgttgacg
                 ctttcgggga ccgaagcatt tgtttcgagc cttgtgaggc cttgttgacg
                 tttcaggga  ccgaaagcat tgtttcggc  cttgtgaggc cttgttgacg
                 ctttcggggg accgaagcat tgtttgagc  cttgtgaggc cttgttgacg
                 tttcggggac cgaaggcatt tgtttcgagc cttgtgaggc cttgttgacg 101                                               150
                 agcattcatg cttgcctcta cggggcatca tggttgtctg gttgacacac
                 agcattcatg cttgcctcta cggggcatca tggttgtctg gttgacacac
                 agcattcatg cttgcctcta cggggcatca tggttgtctg gttgacacac
                 agcattcatg cttgcctcta cggggcatca tggttgtctg gttgacacac
                 agcattcatg cttgcctcta cggggcatca tggttgtctg gttgacacac
                 agcattcatg cttgcctcta cggggcatca tggttgtctg gttgacacac 151                                               200
                 taacaacccc c.gcacaaca tgtgccaagg aaaacaaaac ttaaagggct
                 taacaacccc c.gcacaaca tgtgccaagg aaaacaaaac ttaaagggct
                 taacaacccc cggcacaaca tgtgccaagg aaaacaaaac ttaaagggct
                 taacaacccc cggcacaaca tgtgccaagg aaaacaaaac ttaaagggct
                 taacaacccc cggcacaaca tgtgccaagg aaaacaaaac ttaaagggct
                 taacaacccc cggcacaaca tgtgccaagg aaaacaaaac ttaaagggct 201                                               250
                 tgtgctgtta tgccccgtc. attggtgtgc atactgtgcg ttgcttcttt
                 tgtgctgtta tgccccgtca attggtgtgc atactgtgcg ttgcttcttt
                 tgtgctgtta tgccccgtc. attggtgtgc atactgt.cg ttgcttcttt
                 tgtgctgtta tgccccgtc. attggtgtgc atagtgtgcg ttgcttcttt
                 tgtgctgtta tgccccgtc. attggtgtgc atactgtgcg ttgcttcttt
                 tgtgctgtta tgccccgtca attggtgtgc atactgtgcg ttgcttcttt 251
                 tgtaaacttt
                 tgtaaact~~
                 tgtaaacttt
                 tgtaaacttt
                 tgtaaacttt
                 .gtaaact~~
```

FIG. 1

```
            1                                                     50  SEQ ID No
PAT2062  ~~~RAMRACG  ACCGACAGTA  TGCACA.CCA  ATGACGGGGC  ATAACAGCAC   7
PAT2066  ~~ACAAGAGC  AMGCACAGTA  TGSRCASCMA  ATGACGGGGC  AKAACAVCAC   8
PAT2065  WCAAAARAGC  ACGCACAGTA  TGCMCA..CA  ATGACGGGGC  MTAACAGCAC   9
PAT4048  ~~~~~~~~~~  MAARGCACGC  ACAGTATGCA  CACATRCGGG  G.CATAMGMM  10
PAT5094  ~~~~~~~~~~  ~TMAAGASMG  CMAGTATGCM  ACATGACGGG  C.ATACAGCA  11
PAT5095  ~~~~~~~~~Y  AARAGCACGM  CAGWTGCACA  CATGACGGGG  C.ATACAGCA  12
PAT5096  ~~~~~~~~~~  ~~ARGCACGC  ACAGWTGCAC  ACATGACGGG  G.MTACAGCA  13
PAT4047  ~~~~~~~~YM  AASAGCACGC  ACAGTATGCA  CACATGACGG  G.GCATAMGM  14
PAT4049  ~~~~~~~~~~  ~~~~~~~KWM  ARMGMCGMMG  WKMMCAATRC  G.GGGMWMGM  15
PAT4050  ~~~~~~~~TM  AARAGCACGC  AC.RTWGCMA  CAATGACGGG  GCATACAGMC  16
PAT5097  ~~~~~~~~~~  MAGAGSACGC  ACAGTATGCA  CACATGACGG  GCATACAGCA  17

51                                                    100
PAT2062  AAGCCTTTAA  GTTTTGTTTT  CCTTGGCACA  TKTTGTGCCG  GGGGTTGTTA
PAT2066  AAGCCTTTAA  GYTTTGTTTT  CCTTGGCACA  TKTTGTGCCG  GGGGTTGTTA
PAT2065  AAGCCTTTAA  GTTTTGTTTT  CCTTGGCACA  TKTTGTGCCG  GGGGTTGTTA
PAT4048  R.CCTTTAGT  TT..GTT...  CTTGGMCATK  TTGTGCGGGG  GTTGTAGTGT
PAT5094  C.AGCTTTAG  TT..GTT...  CTTGGCACAT  KTGTGCGGGG  G.TGTAGTGT
PAT5095  C.AGCTTTAG  TTTGTTT...  CTTGGMCATK  TTGTRCGGGG  GTTGTAGTGT
PAT5096  CAAGCTTTAA  GTTTTGT...  TTTCYTGGMC  ATKTTGTRCG  GGGTGTAGT
PAT4047  CAGCCTTTAA  GTTTGTT...  CTTGGMCATK  TTGTGCGGGG  GTTGTA...K
PAT4049  MAGCCTTWAG  TTTGTTT...  TCTTGGMMKT  TTGWCGGGG   GTTGTAGTGT
PAT4050  AAGCCTTTAA  GTTTGTTTTC  TTGGCACATK  TTGTGCGGGG  GTTGTAGTGT
PAT5097  CAGCCTTTAA  GTTTG..TTC  TTGGCACATK  TTGTRCGGGG  GTTGTA..KG 101                                                   150
PAT2062  GTGTGTCAAC  CAGACAACCA  WGRTG.CCCC  GKAGAGGCAR  CMTGRATKCT
PAT2066  GTGTGTCAAC  CAGACAACCA  TGATG.CCCG  TAGAGGCAAG  CATGAATGCT
PAT2065  GTGTGTCAAC  CAGACAACCA  WKRWGCCCCS  KAGAGGCAAG  CMTKAATGCT
PAT4048  GTCACYAGAC  ACATGATGCC  GTAGAGCAGC  ATG.....AT  GCTCGTCACA
PAT5094  GTCACAGACA  ACATGATGCC  .KAGAGCAGC  ATG.....AT  GCTCGTCACA
PAT5095  GTCACAGACA  ACATG.WGCC  GTAGAGCAGC  ATG.....AT  GCTCG.YACA
PAT5096  GTGYACAGAC  ACATGWGCCC  GTAGAGCAGC  ATG.....AT  GCTCG.YACA
PAT4047  GTGTCACARC  ACAYGWGCCC  GY.RAGCARC  MTG.....AT  GCYCGTCACA
PAT4049  GYAACA.GAC  ACATGATGCC  CGWGAGCAG.  MTG.....AT  GCTCGTCACA
PAT4050  GYAACCAGAC  AACATGATGC  CCGTAGAGGC  AAGCATGAAT  GCTCGTCAAC
PAT5097  TGYACCAGAC  AACATGATG.  CCGTAGAGGC  AAGCATGAAT  GCTCGTCACA 151                                                   200
PAT2062  CSTCAACAAR  GCCTCACAAG  GSTCSAAACA  AATGCTTCGG  KCCCCSAAAA
PAT2066  CGTCAACAAG  GCCTCACAAG  GCTCGAAACA  AATGCTTCGG  TCCCYG.AAA
PAT2065  CGTCAACAAR  GCCTCACAAG  GSTCSAAACA  AATGCTTCGG  TCCC..GAAA
PAT4048  RGCTCAC.AG  STCGAACAAT  GCTTCGT.CY  RAGGCAGTAG  TTWTACATGT
PAT5094  GGCTCAC.AG  CTCGAACAAT  GCTCGGTCCS  AAGGCAGTAG  TTATACATGT
PAT5095  GGCTC.M.AG  CTCGAACAAT  GCTCGGTCCC  GAAGCAGTAG  TTWTACATGT
PAT5096  GGCTCAC.AG  STCGAAC.AT  GCTCRGTCCG  AAGGCAGTAG  TTWTACATGT
PAT4047  RGCTCMC.AG  STCGMACAAT  GCTCG..TCY  SMAGCASTAG  TTWTACATGT
PAT4049  RGCTCACARG  STCGAACAAT  GCTCG.....  .TCKAAGCAG  WGTWWCATGT
PAT4050  AGGCTCACAG  CTCGAACAAA  TGCTCGTCCY  RAGGCAGTAG  TTWTACATGT
PAT5097  GGCTCACAAG  GCTCGAACAA  TGCTCGGTCC  RA.GCAGTAG  TTWTACATGT
```

FIG. 3

```
         201                                                     250
PAT2062  GGCCARTAGT TTWTACATGT TCACGGGKCG TTCTGCTATG CAGRTTYGAC
PAT2066  GGSCAGTAGT TTWTACATGT TCACGGGTSG TTCTGCTATG CAGGRTTCGA
PAT2065  RGSCAGTWGT TTWTACATGT TCAC.GGKCG TTCTGCTATG CAGGRTTCGA
PAT4048  CAC.GGGYGT CTGCTAK..C AGRTCGACAW GAWC.TCGCR GTCACYACGR
PAT5094  CAC.GGTCGT CTGCTAT..S AGATCGACAT GATC.TCGCR GTCACTACGA
PAT5095  CAC.GGKCGT CTG.YAT..S AGRTCGACAW GATC.TCGCR GTCACTACGA
PAT5096  CAC.GGKCGT CTGCTAT..S AGRTCGACAT GATCTTCGCA GTCACTACGR
PAT4047  CAC.GGKCGT CTGCTMTGCM GGATCGMCAM TGAYCYCGCM GTCMCTACGG
PAT4049  CAC.GGKCGT CTGCTAKCAG R...TCRCAT GATCTTCGCA GTCACTACGR
PAT4050  CAC.GGKCGT CTGCTAK..C RGRTCGACAT GATCTTCGCA GTCACTACGR
PAT5097  CACGGGTCGT CTGCTAK..C AGATCG.MAT GATCTTCGCA GTTCACTACG 251                                                     300
PAT2062  AATGATC..K MDCCGCMGGR TCACYACGGG AAMCTTTGTA CGCTTTTWC~
PAT2066  CAWGATSHGK CAACSCAGGT TCMCYACRGR AAAMYTTGTA CRCATTTA~~
PAT2065  CAATGATCCT TCCGCAGGKT CACCTACGGR AACCTTGTTA CGACTTTTWM
PAT4048  ACTGTACGMT TWCT~~~~~~ ~~~~~~~~~~ ~~~~~~~~~~ ~~~~~~~~~~
PAT5094  ACTGTACRCT TACT~~~~~~ ~~~~~~~~~~ ~~~~~~~~~~ ~~~~~~~~~~
PAT5095  ACTGTACGAC TTAC~~~~~~ ~~~~~~~~~~ ~~~~~~~~~~ ~~~~~~~~~~
PAT5096  ACTGTACAGM TTACGTC~~~ ~~~~~~~~~~ ~~~~~~~~~~ ~~~~~~~~~~
PAT4047  AACMYGTASA CTTA~~~~~~ ~~~~~~~~~~ ~~~~~~~~~~ ~~~~~~~~~~
PAT4049  ACTGTASACT TACT~~~~~~ ~~~~~~~~~~ ~~~~~~~~~~ ~~~~~~~~~~
PAT4050  AACWTGTACG ACTTAC~~~~ ~~~~~~~~~~ ~~~~~~~~~~ ~~~~~~~~~~
PAT5097  GAACTGTACG AMTTTTAY~~ ~~~~~~~~~~ ~~~~~~~~~~ ~~~~~~~~~~

301
PAT2062  ~
PAT2066  ~
PAT2065  T
PAT4048  ~
PAT5094  ~
PAT5095  ~
PAT5096  ~
PAT4047  ~
PAT4049  ~
PAT4050  ~
PAT5097  ~
```

FIG. 3 (continued)

```
            1                                                      50  SEQ ID#
PAT1_6053  RWAGTGCACG TACATGCGCA CA.CGCGAAC GGGGCGCAAT AGCACGGGCC   18
PAT1_6055  ~~~GTGCACG TACATGCGCR CR.CGCGAAC GGGGCGCAAT AGCACGGG.C   19
PAT1_6054  ~WAGTGCACG TACATGCGCA CMCCGCGAAC GGGGCGCAAT AGCACGGG.C   20
PAT1_6052  ~~WGTGCACG WCAATGCGCA CA.CGCGAAC GGGGCGCAAT AGCACGGG.C   21

51                                                    100
PAT1_6053  CTTTAARTTT ARTTTTCCTT GGCACGTACG GTGCCGGGGG TTTGTTATTG
PAT1_6055  CTTTAAGTTT AGTTTTCCTT GGCACGTACG GTGCCGGGGG TTTGTTATTG
PAT1_6054  CTTTAAGTTT AGTTTTCCTT GGCACGTACG GTGCCGGGGG TTTGTTATTG
PAT1_6052  CTTTAAGTTT AGTTTTCCTT GGCACGTACG GTGCCGGGGG TTTSTTATTG 101                                                   150
PAT1_6053  TGTCAACATG TATCCATGAT GCCCCATATG TATGGTGCAG CCATAAACAC
PAT1_6055  TGTCAACATG TATCCATGAT GCCCCRTATG TATGGTGCAG CCATAAACAC
PAT1_6054  TGTCAACATG TATCCATGAT GCCCCATATG TATGGTGCAG CCATAAACAC
PAT1_6052  TGTCAACATS TATCCATGAT GCCCRTCATG TATGGTGCAG CCATAAAMAC 151                                                   200
PAT1_6053  ACGTCGACAA GGCCTCRCGA GGCTCGAAAC ATAAGCTCCG GTCCTCGCTC
PAT1_6055  ACGTCGACAA GGCCTCACGA GGCTCGAAAC ATAARCTCCG GTCCTCGCTC
PAT1_6054  ACGTCGACAA GGCCTCACGA GGCTCGAAAC ATAAGCTCCG GTCCTCGCTC
PAT1_6052  ACGTCGACAA GG.CTCSCGM GGSTCGMAAC ATAARSYCCS GTCCTC.VTC 201                                                   250
PAT1_6053  GGTCATGTGT TTTTACTTGT TCACGGGTCG TTCTGCTATG CA.GGGTTCG
PAT1_6055  GGTCATGTGT TTTTACTTKT TCACGGGTCG TTCTGCTATG .M.GGGTTCG
PAT1_6054  GGTCATGTGT TTTTACTTGT TCACGGGTCG TTCTGCTATG CAGGGKTTCG
PAT1_6052  GGTCATGTG. TTTTACYTGT TCACCGSGKC GSTTCTGCYA TGMGGGGTCG 251                                                   300
PAT1_6053  ACAATGATCY AHCGCAGGTT CACTAC.... GGAAACTTGT ACGACTWTAA
PAT1_6055  AMAATGATCC TDCCGCAGTT TMCTAC.... GAAAACTTGT WACAATTTWA
PAT1_6054  AMAATGATCC STVNSGCAGG TTCMCCYACG GAAACCTKGT AMGACTTTTA
PAT1_6052  MCCMTGAYCC YWCCCGCMGG KCMCCYMCCG GSGACCCTST WCCGMCYTTT

301
PAT1_6053  C
PAT1_6055  ~
PAT1_6054  C
PAT1_6052  A
```

FIG. 4

```
         1                                                    50 SEQ ID#
PAT2062  VCWTCTWRTG TCTGGTTGGG GSGGAGATTG GTCTCC..GT GCACTTGCAT  22
PAT2066  YATTTAGATG TCTGGTTGGG GCGGAGATTG GTCTCCCGTG CCACTTGCAT  23
PAT2063  ~~~~~~~~~~ TGYTGGTGGG GCGGAGATTG GTCTCC..GT GCACTTGCAT  24

51                                                   100
PAT2062  GGTTGACCTA AATATGAGTC TCCTCACGAG AGACGCACGG CTAGTGGTGG
PAT2066  GGTTGACCTA AATATGAGTC T.CTCACGAG AGACGCACGG CTAGTGGTGG
PAT2063  GGTTGACTAA TAT....GRT CTCTCACG.. .RRMGCACGG CTAGTGGTGG 101                                                  150
PAT2062  TTGATAACAC AGTCGTCTCG TGCCGTACGT TTATGTTTGT GAGTGTCTAG
PAT2066  TTGATAACAC AGTCGTCTCG TGCCGTACGT TTATGTTTGT GAGTGTCTAG
PAT2063  TTGAT.ACAC AGTCGTCTCG TG.CGTACGT TTATGTTTGT GAGTGTCTAG 151                                                  200
PAT2062  ACTTGTGAAA AAMCTGACGC GTCGTCTTCA GATGATGCTT CGATCGCGAC
PAT2066  ACTTGTG.AA AACCTGACGC GTCGTCTTCA GATGATGCTT CGATCGCGAC
PAT2063  ACTTGTG... AAACTGACGC GTCGTCTTCA GATKATGCTT CG.WCGCGAC 201                                                  250
PAT2062  CCCA.GGTCA GGSGGGACTA CCSCYGAGTT TAARCATATC AATAARCGGA
PAT2066  CCCAGGGTCA GGSGGGACTA CCCGCTGAGT TAAGCATATC AATAAGSGGA
PAT2063  CC...AGTCA GSGGGMTACC SCTGRTTWAS ATATMAWASG GA~~~~~~~~
```

FIG. 5

```
                    1                                                    50 SEQ ID #
1-6053    ~~~~~~~~aA GTGCACGTAC .ATGCGCACA cCGCGAAC.G GGGCGCAATA    25
1-6055    ~~~~~~~~aa GTGCACGTAC .ATGCGCaCa cCGCGAAC.G GGGCGCAATA    26
1-6054    ~~~~~~~~aa GTGCACGTAC AaTGCGCACA CcGCGAAC.G GGGCGCAATA    27
1-6052    ~~~~~~~AAG TtGCACGTAC AATGCGCACA CcGCGAAC.G GGGCGCAATA    28
1-1105    ttACaAaAgA aGCAACGCAC AGTATgCaCA CCAATGAC.G GGGCATAAcA    29
1-5074    ~TACAAAAGA AGCAACGCAC AGTATGCACA CCAATGAC.G GGGCATAACA    30
1-3017    ~~~caaAaGA AGcAaCGCAC AGTATGCACA CcAaTRAC.G GGGCatAaca    31
1-4042    ~~acaaaagA aGcAacgCAC AGTATGCACA cCAATGAC.G GGGCATAACA    32
1-3016    ~~~caaAaGA agcAaCGCAC AGTATGCACA CcAATRAC.G GGGCATAACA    33
1-2070    TTaCaaAAGA AGCAACGCAC AGTATGCACA CCAATGAC.G GGGCATAACA    34
1-3061    ~tacaaAaGA agCAaCGCAC AGTAtgCACA CcAaTGAC.G GGGCatAaCA    35
1-1107    ttaCAAAAGA AGCAACGCAC AGTATGCACA CCAATGAC.G GGGCATAACA    36
1-4043    ~~~~~~~AGA agCAaCGCAC AgTATGCACA CCAATGAC.G GGGCATAACA    37
1-4035    ttacAaAaGA aGCAaCGCAC AGTATGCACA CcAATGAC.G GGGCATAACA    38
1-4049    TtACAAAaGA agCAaCGCAC AGTATGCACA CCAATGAC.G GGGCATAACA    39
1-4050    TTACAAAagA agCAaCGCAC AGTATGCACA CCAATGAC.G GGGCATAACA    40
1-2068    ttacaaAAGA AGCAACGCAC AGTATGCACA CCAATGAC.G GGGCATAACA    41
1-3059    ~~~~~~~~~~ ~~~~ACGCAC AGTATGCACA CcAATRAC.G GGGCAtAaCA    42
1-4031    ~~~~~~~~~~ aGCaaCGCAC AGTATGCACA CCAATGAC.G GGGCATAACA    43
1-4038    ~~~~~~~aGA aGCAaCGCAC AGTATGCACA CCAATGAC.G GGGCATAACA    44
1-4041    ~~~~aAAaGA aGCAacGCAC AGtatgCACA CcAAtgAC.G GGGCAtaACA    45
1-4047    TTACAaaAgA AGCaaCGCAC AGTATGCACA CcAATGAC.G GGGCATAACA    46
1-5094    TtacAAAagA AGCAaCGCAC AGTATGCACA CCAATGAC.G GGGCATAACA    47
1-4037    TTacAaAaGA aGCAaCGCAC AGTATGCACA CCAATGAC.G GGGCATAACA    48
1-3060    ~TACAaaAgA AGcAacGcAC AGTATGCACa CCaATRAC.G GGGCATAaCA    49
1-4032    ~~~~~~~~~~ agcAaCGCAC AGTATGCACA ccAATGAC.G GGGCATAACA    50
1-4046    ~taCAaAaGA aGCAaCGCAC AGTATGCRCA CCAATGAC.G GGGCATAACA    51
1-4048    ttACAaAAGA AGCAACGCAC AGTATGCACA CCAATGAC.G GGGCATAACA    52
1-3058    ~tacAaAaGA aGCAacGCAC AGTATGCACA CcAaTRAC.G GGGCATAaCA    53
1-4044    TtACAAAAGA AGCAACGCAC AGTATGCACA CCAATrAC.G GGGCATAACA    54
1-5076    TTacAAaAGA AGCAACGCAC AGTATGCACA CCAATGAC.G GGGCATAACA    55
1-2066    ~~ACAaAaGA aGCAacGCAC AGTATGcaCA cCAATGAC.G GGGCAtAACA    56
1-5097    ~tacAaAAGA AGCAaCGCAC AGTATGCACA CCAATGAC.G GGGCATAACA    57
1-2062    ~~~caaAaga AgCAaCgcAC AGTATGCACA CCAATGAC.G GGGCATAACA    58
1-3020    ~~AcAAAAGA AGcaACGCAc AGTATGCACA CCAATGAC.G GGGCATAaCA    59
1-2064    ttACAAAAGA AGCAaCGCAC AGTATGCACA CCAATGAC.G GGGCATAACA    60
1-2102    ~~~~aaANga AgCAaCgCAC AGTATGCACA CCAATGAC.G GGGCATAACA    61
1-3057    ~tACAaaAGa aGCAACgCAC AGTATGcACA CCAATRAC.g GGGCATAACA    62
1-2065    ~~~CAaAaGA AGCAACGCAC AGTATGCACA CcAATGAC.G GGGCATAACA    63
1-2067    TTacAAAAGA AGCAACGCAC AGTATGCACA CCAATGAC.G GGGCATAACA    64
1-4034    ~~~cAaAagA aGcAaCGCAC AgTatGCaCA CCAATGAC.G GGGCATAacA    65
1-2072    ~~aCaAAaGA AGCAACGCAC AGTATGCAcA CCAATGAC.G GGGCATAACA    66
1-5095    ~~tCAAAAGA AGCAaCGCAC AGTATGCACA CcAATGAC.G GGGCATAaCA    67
1-2111    ~~~~~~~~~~ ~~~~~~~~~C AGTATGCACA CCAATGAC.G GGGCATAACA    68
1-3015    ~taCAaAaGA aGCAaCGCAC AGTATGCACA CCAATRAC.G GGGCATAACA    69
1-3018    ~~aCaAaAGA agcAaCGCAC AGTATGCACA CCAATRAC.G GGGCATAACA    70
1-2100    ~tACAAaAGA AGCAACGCAC AGTATGCACA CCAATGAC.G GGGCATAACA    71
1-2104    ~~~CAaAAGA AGCAAcGCAc AGTATGCaCA CCAATGAC.G GGGCATAACA    72
1-5075    ~tACAAaAGA AGCAACGCAC AGTATGCACA CCAATGAC.G GGGCATAACA    73
1-5096    ~tacAaaAgA aGcAaCGCAC AGTATGCACA CCAATGAC.G GGGCATAACA    74
1-5077    ~tACAAAAGA AGCAACGCAC AGTATGCACA CCAATGAC.G GGGCATAACA    75
```

FIG. 6

|  |  | SEQ ID# |
|---|---|---|
| 1-5073 | ~~~CAAAaGA AGCaaCGCAC AGTATGCACA CCAaTGAC.G GGGCATAACA | 76 |
| 1-3019 | ~~~~~~~~~~ ~~CAaCGCAC AGTATGCACA CcAATRAC.G GGGCATAACA | 77 |
| 1-4039 | ~~~~~~~~~~ ~~~cacGcAC AGTAtGCACA CCAATGACGG GGGCATAACA | 78 |
| 1-3056 | ~tACAaAaGa aGCaaCGCAC AGTATGCa.A CcAATRAc.G GGGcaTAaCA | 79 |
| 1-2071 | ~~~CAAAAGA AgCAaCGCAC AGTATGCACA CCAATGAC.G GGGCATAACA | 80 |
| 1-2101 | ~tACAAaAGA aGCaACGCAC AGTATGCACA CCAATGACGG GCGCATAACA | 81 |

```
           51                                                100
1-6053     GCAC.GGG.C CTTTAAgTTT AgTTTTCCTT GGCACGTACG GTGCCGGGGG
1-6055     GCAC.GGG.C CTTTAAGTTT AGTTTTCCTT GGCACGTACG GTGCCGGGGG
1-6054     GCAC.GGG.C CTTTAAGTTT AGTTTTCCTT GGCACGTACG GTGCCGGGGG
1-6052     GCAC.GGGCc CTTTAAGTTT AGTTTTCCTT GGCACGTACG GTGCCGGgGG
1-1105     gCACAaG.CC CTTTAAGTTT TGTTTTCCTT GGCACATKTT GTGCCGGGGG
1-5074     GCACAAG.CC CTTTAAGTTT TGTTTTCCTT GGCACATKTT GTRCCGGGGG
1-3017     GcaCaaG.CC cTTTAaGTtT TGTTTTCcTT GGCACATKTT GTGCcGGGGG
1-4042     GCACAAG.Cc CTTTAAGTTT TGTTTTCCTT GGCACATKTT GTGCCGGGGG
1-3016     GCACAAG.Cc CTTTAAGTTT TGTTTTCCTT GGCACATKTT GTGCCGGGGG
1-2070     GCACAAG.CC CTTTAAGTTT TGTTTTCCTT GGCACATKTT GTGCCGGGGG
1-3061     GCACAAG.Cc CTTTAaGTTT TGTTTTCcTT GGcacaTgTT GTGCcGGGGG
1-1107     GCACAAG.CC CTTTAAGTTT TGTTTTCCTT GGCACATKTT GTGCCGGGGG
1-4043     GCACAAG.Cc CTTTAAGTTT TGTTTTCCTT GGCACATgTT GTGCCGGGGG
1-4035     GCACAAG.Cc CTTTAAGTTT TGTTTTCCTT GGCACATKTT GTGCCGGGGG
1-4049     GCACAAG.Cc cTTTAAGTTT TGTTTTCCTT GGCACATKTT GTRCCGGGGG
1-4050     GCACAAG.Cc CTTTAAGTTT TGTTTTCCTT GGCACATKTT GTGCCGGGGG
1-2068     GCACAAG.CC CTTTAAGTTT TGTTTTCCTT GGCACATKTT GTGCCGGGGG
1-3059     GCACAAG.CC CTTTAAGTTT TGTTTTCCTT GGCACATKTT GTGCCGGGGG
1-4031     GCACAAG.CC CTTTAAGTTT TGTTTTCCTT GGCACATKTT GTGCCGGGGG
1-4038     GCACAAG.Cc CTTTAAGTTT TGTTTTCCTT GGCACATKTT GTGCcGGGGG
1-4041     GCACAaG.CC CTTTAaGTTT tgTTTTCCTt GgCACAtkTt gtgCcGGGGg
1-4047     GCACAAG.Cc CTTTAAGTTT TGTTTTCCTT GGCACATgTT GTGCCGGGGG
1-5094     GCACAAG.Cc CTTTAAGTTT TGTTTTCCTT GGCACATgTT GTGCCGGGGG
1-4037     GCACAAG.Cc CTTTAAGTTT TGTTTTCCTT GGCACATgTT GTGCCGGGGG
1-3060     GCACAAG.CC CTTTAagTTT TGTtTTcCTT GGCACATKTt gTGCCGGGGG
1-4032     GCACAAG.Cc CTTTAAGTTT TGTTTTCCTT GGCACATKTT GTGCCGGGGG
1-4046     GCACAAG.Cc CTTTAAGTTT TGTTTTCCTT GGCACATgTT GTGCCGGGGG
1-4048     GCACAAG.Cc CTTTAAGTTT TGTTTTCCTT GGCACATKTT GTGCCGGGGG
1-3058     GCACAAG.Cc CTTtaAGTtT TGTTTTcCTT GGCACATkTT GTGcCGGGGG
1-4044     GCACAAG.CC CTTTAAGTTT TGTTTTCCTT GGCACATKTT GTGCCGGGGG
1-5076     GCACAAG.CC CTTTAAGTTT TGTTTTCCTT GGCACATKTT GTRCCGGGGG
1-2066     gCACAAG.Cc CTTTAAGtTT TGTTTTCCTT GGCACATgTT GTGCCGGGGG
1-5097     GCACAAG.Cc CTTTAAGTTT TGTTTTCCTT GGCACATgTT GTRCCGGGGG
1-2062     GCACAAG.Cc CTTTAAGTTT TGTTTTCCTT GGCACATKTT GTGCCGGGGG
1-3020     GCaCAAG.CC CTTTAAGTTT TGTTTTCCTT GGCACATKTT GTGCCGGGGG
1-2064     GCACAAG.CC CTTTAAGTTT tGTTTTCCTT GGCACATKTT GTGCCGGGGG
1-2102     GCACAAG.cC CTTTAAGTTT TGTTTTCCTT GGCACATKTT GTGCCGGGGG
1-3057     GCACAAG.CC CTTTAAGTTT TGTTTTCCTT GGCACATKTT GTGCCGGGGG
1-2065     GCACAAG.Cc CTTTAAGTTT TGTTTTCCTT GGCACATKTT GTGCCGGGGG
1-2067     GCACAAG.CC CTTTAAGTTT TGTTTTCCTT GGCACATKTT GTGCCGGGGG
1-4034     GCACAAG.Cc CTtTAaGTTT TGTTTTCCTT GGCACATgTT GTGCCGGGGG
1-2072     GCACAAG.CC CTTTAAGTTT TGTTTTCCTT GGCACATKTT GTGCCGGGGG
1-5095     GCACAAG.Cc CTTTAAGTTT TGTTTTCCTT GGCACATgTT GTRCCGGGGG
1-2111     GCACAAG.CC CTTTAAGTTT TGTTTTCCTT GGCACATrtT GTGCCGGGGG
1-3015     GCACAAG.Cc CTTTAAGTTT TGTTTTCCTT GGCACATKTT GTGCCGGGGG
1-3018     GCACAAG.CC CTTTAAGTTT TGTTTTCCTT GGCACATKTT GTGCCGGGGG
```

FIG. 6 (Continued)

```
1-2100  GCACAAG.CC CTTTAAGTTT TGTTTTCCTT GGCACATTTT GTGCCGGGGG
1-2104  GCACAAG.CC CTTTAAGTTT TGTTTTCCTT GGCACATKTT GTGCCGGGGG
1-5075  GCACAAG.CC CTTTAAGTTT TGTTTTCCTT GGCACATKTT GTGCCGGGGG
1-5096  GCACAAgCCc CtTTAAGTTT TGTTTTCCtT GGCACATKTT GTRCCGGGGG
1-5077  GCACAAG.CC CTTTAAGTTT TGTTTTCCTT GGCACATKTT GTRCCGGGGG
1-5073  gcACAAG.CC CTTTAAGTTT TGTTTTCCTT GGCACATKTT GTGCCGGGGG
1-3019  GCACAAG.CC CTTTAAGTTT TGTTTTCCTT GGCACATKTT GTGCCGGGGG
1-4039  GCACAAG.Cc CTTTAAGTTT TGTTTTCCTT GGCACATKTT GTRCCGGGGG
1-3056  GCACAAG.Cc CTTTAaGTTT TGTTTTCcTT GGcaCATKTT GTGCcGGGGG
1-2071  GCACAAG.CC CTTTAAGTTT TGTTTTCCTT GGCACATKTT GTGCCGGGGG
1-2101  GCACAAGCCC TTTAAGTTTT GtTTTCCTTG AGCACATKTT GTGCCGGGGG 101                                                150
1-6053  TTTGTTATTG TGTCAACATG TATCCATGAT GCCCCrTATG TATGGTGCAG
1-6055  TTTGTTATTG TGTCAACATG TATCCATGAT GCCCCRTATG TATGGTGCAG
1-6054  TTTGTTATTG TGTCAACATG TATCCATGAT GCCCCrTATG TATGGTGCAG
1-6052  TTTgTTaTTG TGTCaaCATg TATCCATGAT GCccCRTATG TATGGTGCAG
1-1105  TTGTTAgTGT GTCAACCAGA CAACCATGAT GCCCCGTA.. ...GAGGCAA
1-5074  TTGTTAgtGT GTCAACCAGA CAACCATGAT GCCCCGTA.. ...GAGGCAA
1-3017  TTGTtAGTGT GTCAacCAGA CAAccATgat GCcCCGTA.. ...GAGGCAa
1-4042  TTGTTAGTGT GTCAACcAGA CAACCATGAT GCCcCGTA.. ...GAGGCAA
1-3016  TTGTTAGTGT GTCAacCAGA CAACCATGAT GCCcCGTA.. ...GAGGCAa
1-2070  TTGTTAgTGT GTCAACCAGA CAACCAtgat gcCCCGtA.. ...GAgGcaA
1-3061  TtGTTAgtGT GtcaACCAGA CAaCCATGAT GCcCCGTA.. ...GAGGCAa
1-1107  TTGTTAGTGT GTCAACCAGA CAACCATGAT GCCCCGTA.. ...GAGGCAA
1-4043  TTGTTAGTGT GTCAACCAGA CAACCATGAT GCcCCGTA.. ...GAGGCAa
1-4035  TTGTTAGTGT GTCAACCAGA CAACCATGAT GCcCCGTA.. ...GAGGCAA
1-4049  TTGTTAGTGT GTCAACCAGA CAACCATGAT GCcCCGTA.. ...GAGGCaA
1-4050  TTGTTAGTGT GTCAACCAGA CAACCATGAT GCcCCGTA.. ...GAGGCAA
1-2068  TTGTTAgTGT GTCAACCAGA CAAcCatgaT gcCCCGta.. ...gAGGcaA
1-3059  TTGTTAGTGT GTCAACCAgA CAACCATGAT GCcCCGtA.. ...GAGGCAa
1-4031  TTGTTAGTGT GTCAACCAGA CAACCATGAT GCCCCGTA.. ...GAGGCAA
1-4038  TTGTTAGTGT GTCAACCAGA CAACCATGAT GCCCCGTA.. ...GAGGCAA
1-4041  TtgTTAgtgt gTcAacCAGA CAACCATGAT GCCCcgTA.. ...GAGGCAA
1-4047  TTGTTAGTGT GTCAACCAgA CAACCAtGAT GCcCCGtA.. ...GAGGCAA
1-5094  TTGTTAGTGT GTCAACcAGA CAACCATGAT GCCcCGTA.. ...GAGGCAA
1-4037  TTGTTAGTGT GTCAACCAGA CAACCATGAT GCCCCGTA.. ...GAGGCAA
1-3060  TTGTTAGTGT GTCAACCAGA CAaCCATGAT GCcCCGTA.. ...GAGGCAA
1-4032  TTGTTAGTGT GTCAACCAGA CAACCATGAT GCCCCGTA.. ...GAGGCAA
1-4046  TTGTTAGTGT GTCAACCAGA CAACCATGAT GCCCCGTA.. ...GAGGCAA
1-4048  TTGTTAGTGT GTCAACYAGA CAACCATGAT GCCCCGtA.. ...GAGGCAA
1-3058  TTGtTAGTGT GtcAaCCAGa cAACCAtgAT GCcCCGTA.. ...GAGGCAa
1-4044  TTGTTAgTGT GTCAACCAGA CAACCATGAT GCCCCGTA.. ...GAGGCAA
1-5076  TTGTTAgTGT GTCAACCAGA CAACCATGAT GCCCCgTA.. ...GAGGCAA
1-2066  TTGTTAGTGT GTCAACCAGA CAACCATGAT GCcCCGTA.. ...GAGGCAA
1-5097  TTGTTAGTGT GTCAACCAGA CAACCATGAT GCcCCGTA.. ...GAGGCAA
1-2062  TTGTTAGTGT GTCAACCAGA CAACCAtGaT GCCCCGtA.. ...GAGGCaa
1-3020  TTGTTAGTGT GTCAACCAGA CAACCATGAT GCCCcgtA.. ...GAGGCAA
1-2064  TTGTTAGTGT GTCAACCAGA CAACCATGAT GCCCCGTA.. ...GAGGCAA
1-2102  TTGTTAgtGT GTCAACCAGA CAACCATGAT GCCCCGTA.. ...GAGGCaA
1-3057  TTGTTAgTGT GTCAACCAGA CAACCATGAT GCCCCGTA.. ...GAGGCAA
1-2065  TTGTTAGTGT GTCAACCAGA CAACCAagat GCCCCgtA.. ...GAGGCAA
1-2067  TTGTTAgTGT GTCAACCAGA CAACCATGAT GCCCCGTA.. ...gAGGCAA
1-4034  TTGTTAGTGT GTCAaCCAGA CAACCATGAT GCCcCgTA.. ...GAGGCAA
1-2072  TTGTTAgTGT GTCAACCAGA CAACCATGAT GCCCCGTA.. ...GAGGCAA
```

FIG. 6 (Continued)

```
1-5095   TTGTTAGTGT GTCAACCAGA CAACCATGAT GCCCCGTA.. ...GAGGCAA
1-2111   TTGTTAGTGT GTCAACCAGA CAACCATGAT GCCCCGTA.. ...GAGGCAA
1-3015   TTGTTAGTGT GTCAACCAGA CAACCATGAT GCcCCGTA.. ...GAGGCAA
1-3018   TTGTTAGTGT GTCAACCAGA CAaCCATGAT GCCCcgTA.. ...GAGGCAA
1-2100   TTGTTAgTGT GTCAACCAgA CAACCATRAT GCCCCGTA.. ...gAgGCAA
1-2104   TTGTtAgTGT GTCAAcCAGA CAACCATGAT GCCCCGTA.. ...gAgGCAA
1-5075   TTGTTAgTGT GTCAACCAGA CAACCATGAT GCCCCGTA.. ...GAGGCAA
1-5096   tTGTTAGTGT GTCAACCAGA CAACCATGAT GCcCCGTA.. ...GAGGCAA
1-5077   TTGTTAGTGT GTCAACCAGA CAACCATGAT GCCCCGTA.. ...GAGGCAA
1-5073   TTGTtAgtGT GTCAACCAGA CAACCAtGAT GCCcCGTA.. ...gAGGCAA
1-3019   TTGTTAGTGT GTCAACCAGA CAACCATGAT GCcCCGTA.. ...GAGGCAa
1-4039   TTGTTAGTGT GTCAACCAGA CAACCATGAT GCcCCGTA.. ...GAGGCaA
1-3056   TtGTtAGTGT GTCAaCCAGA CAaCCATGAT GCcCcGTA.. ...GAGGCaA
1-2071   TTGTTAgTGT GTCAACCAGA CAAcCATGAT GCCCCGTA.. ...gAgGcaA
1-2101   TTGTTAgTGT GTCAACCAGA CAACCATGAT GCCCCGTA.. ...GAGGCAA 151                                                200
1-6053   CCATAAACAC ACGTCGAC.A AGGCCTCaCG AGGCTCGAAA CATAAGC.TC
1-6055   CCATAAACAC ACGTCGAC.A AGGCCTCACG AGGCTCGAAA CATAAgC.TC
1-6054   CCATAAACAC ACGTCGAC.A AGGCCTCACG AGGCTCGAAA CATAAGC.TC
1-6052   CCATAAAcAC ACGTCGAC.A AGGCcTCGCG aGGcTCGAAA CATAAGc.tC
1-1105   GCATGAAT.G CTCGTCAACA AGGCCTCACA AGGCTCGAAA C.AAATGCTT
1-5074   gCATGAATAG CTCGTCAACA AGGCCTCACA AGGcTCgAAA CAAAATGCTT
1-3017   GCATGAaTGC TCGTCAaC.A aGGCcTCACa AGGcTCGAaA c.AaATGctT
1-4042   GCATGAATGC TCGTCAAC.A AGGCCTCACA AGGcTCGAAA CAAAATGCTT
1-3016   gCATGAaTGC TCGTCAAC.A AGGCCTCACA AGGcTCGAaA C.AaATGCTT
1-2070   gcaTgaATGc TCGtcaAc.A AGG.CTCACA AGGcTCgAAA caAATGc.TT
1-3061   gCATGAaTGC TCGTCaaC.A AGG.CTCACA AGGCTCRAaA CAAATGC.TT
1-1107   GCATGAATGC TCGTCAAC.A AGGCCTCACA AGGCTCGAAA CAAATGC.TT
1-4043   GCATGAATGC TCGTCAAC.A AGGcCTCACA AGGCTCGAAA CAAATgC.TT
1-4035   GCATGAATGC TCGTCAAC.A AGGCCTCACA AGGCTCGAAA CAAATGC.TT
1-4049   gCATGAATGC TCGTCAAC.A AGGcCTCACA AGGCTCGAAA CAAATGC.TT
1-4050   GCATGAATGC TCGTCAAC.A AGGCCTCACA AgGCTCGAAA CAAATGC.TT
1-2068   gCaTgAATGc TCGtcAAC.A AgGcCTCACa AgGcTCGAAA caAATGC.TT
1-3059   GCATGAATGC TCGTCAAC.A AGGCCTCaCA AGGCTCgaAa caAaTGC.TT
1-4031   GCATGAATGC TCGTCAAC.A AGGCCTCACA AGGCTCGAAA CAAATGC.TT
1-4038   GCATGAATGC TCGTCAAC.A AGGCCTCACA AGGCTCGAAA CAAATGC.TT
1-4041   GCATGAATGC TCGTCAAC.A AGGCCTCACA AGGCTCGAAA CAAATGC.TT
1-4047   GCaTGAATGC tCGTCAAC.A AGGCCTCACA AgGCTCGaAA CAAATGC.Tt
1-5094   GCATGAATGC TCGTCAAC.A AGGCCTCACA AGGCTCGAAA CAAATGC.TT
1-4037   GCATGAATGC TCGTCAAC.A AGGCCTCACA AGGCTCGAAA CAAATGC.TT
1-3060   GCATGAATGC TCGTCAAC.A AGGCCTCAcA AGGCTCGAAA CAAATGCTTT
1-4032   GCATGAATGC TCGTCAAC.A AGGCCTCACA AGGCTCGAAA CAAATGC.TT
1-4046   GCATGAATGC TCGTCAAC.A AGGcCTCACA AGGCTCGAAA CAAATGC.TT
1-4048   gCATGAATGC TCGTCAAC.A AGGCCTCACA AGGcTCGAAA CAAATGC.TT
1-3058   GCATGAaTGC TCGTCAaC.A AGGCcTCacA AGgcTCGAaA CAaATGC.Tt
1-4044   GCaTGAATGC TCGTCAAC.A AGGCCTCACA AgGCTCgAAA CAAATGC.TT
1-5076   gCATGAATGC TCGTCAAC.A AgGcCTCACA AGGCTCGAAA CAAATGC.TT
1-2066   GCATGAATGC TCGTCAAC.A AGGCCTCACA AGGCTCGAAA CAAATGC.TT
1-5097   GCATGAATGC TCGTCAAC.A AGGCCTCACA AGGCTCGAAA CAAATGC.TT
1-2062   gCaTGaATgC TCgTCAAC.A AgGCCTCACA AGGCTCgAAA CAAATGC.TT
1-3020   GCATGAATGC TCGTCAAC.A AgGcCTCACA AgGCTCGAAA CAAATGC.TT
1-2064   GCATGAATGC TCGTCAAC.A AgGCCTCACA AGGCTCGAAA CAAATGC.TT
1-2102   GCaTGaATGC TCGTCAAC.A AgGcCTCACA AGGcTCGAAA CAAATGC.TT
1-3057   GCATGAATGC TCGTCAAC.A AGGcCTCACA AGGcTCGAAA CAAATgC.TT
```

FIG. 6 (Continued)

```
1-2065    GCaTgAATGC TCGTCAAC.A AgGCCTCACA AGGcTCgAAA CAAATGC.TT
1-2067    GCATGAATGC TCGTCAAC.A AgGCCTCACA AgGCTCGAAA CAAATGC.TT
1-4034    GCATGAATGC TCGTCAAC.A AGGCCTCACA AGGCTCGAAA CAAATGC.TT
1-2072    GCATGAATGC TCGTCAAC.A AGGCCTCACA AGGCTCGAAA CAAATGC.TT
1-5095    GCATGAATGC TCGTCAAC.A AGGCCTCACA AGGCTCGAAA CAAATGC.TT
1-2111    GCATGAATGC TCGTCAAC.A AGGCCTCACA AGGCTCGAAA CAAATGC.TT
1-3015    GCATGAATGC TCGTCAAC.A AGGCCTCACA AGGCTCGAAA CAAATGC.TT
1-3018    gCATGAATGC TCGTCAAC.A AGGcCTCACA AgGCTCGAAA CAAATGc.tT
1-2100    gCATGAATRC TCGTCAAC.A AgGcCTCACA AGGcTCGAAA ACaAATGCTT
1-2104    gCATGAAtGC TCGTcAAc.A AgGCCTCACA AgGCTCGaAA ACAAAtGCTT
1-5075    gCATGAATGC TCGTCAAC.A AGGGCCTCAcA AGGcTCGAAA CAAATGC.TT
1-5096    GCaTGAATGC TCGTCAAC.A AGGcCTCACA AGGcTCGAAA CAAATGC.TT
1-5077    GCATGAATGC TCGTCAAC.A AGGCCTCACA AGGcTCGAAA CAAATGC.TT
1-5073    gCaTGAaTGC tCGTCAACAA AGGcCtCACA AGGcTCGAAA CAAAATGCTT
1-3019    gCATGAATGC TCGTCAAC.A AGGCCTCACA AGGcTCGAAA cAAATGC.TT
1-4039    GCATGAATGC TCGTCAAC.A AGGCCTCACA AGGCTCGAAA CAAATGC.TT
1-3056    GCATGAaTGC TCGTCAaC.a AGGCcTCa.a AgGCTCGAaA CAAaTGC.Tt
1-2071    gCaTGAATGC TCGTCAACAA AGGCCTCACA AGGCTCgAAA cAAAtGC.TT
1-2101    gCaTGaATGC TCGTCAAC.A AGGCCTCAcA AGGcTCGAaA aAAATGC.TT 201                                                250
1-6053    CGGTCCTCGC TCGGTCATGT GTTTTTACTT GTTCACGGGT C.GTTCTGCT
1-6055    CGGTCCTCGC TCGGTCATGT GTTTTTACTT gTTCACGGGT C.GTTCTGCT
1-6054    CGGTCCTCGC TCGGTCATGT GTTTTTACTT GTTCACGGGT C.GTTCTGCT
1-6052    CgGTCCTCgc TCGGtCATGT G.TTTTACtT GTTCaCgGgt C.GTTCTGCt
1-1105    CgGTCcCCGa aAGGCcAgTA GTTTTTACAt GTTCACGGGt C.GTTCTGCt
1-5074    CGGTCCCCgA AAGGCCAGTA gTTTWTACAT GTTCACGGGt C.GTTCTGCt
1-3017    CGgTCcCcGA aAGGCcaGTA GTtTwTACAT G.TCACGGgt C.GTtCTGCT
1-4042    CGGTCCCCGA AASGCCAGTA GTTTwTACAT G.TCACGGGT C.GTTCTGCT
1-3016    CGGtCCcCGA AAGGCCAGTA GTTWTACΛTG T.TCACGGGt C.G.TCTGCT
1-2070    cGGtcCCCgA AAgGcCAGTA gTTTATACAt GtTCACGGGt C.gtTCTGCt
1-3061    CGgtCcCcGA aAGGCcAGta GTtTwTACAT G.TCACGGGT C.GTTCTGCT
1-1107    CGGTCCCCGA AAGGCCAgtA GTTTTTACAT GTTCACgGGt C.GTTCTGCT
1-4043    CGGTCCCYGA AAbGCCAGTA GTTTWTACAT GTTCACGggt C.GTTCTGCT
1-4035    CGGTCCCyRA AAbGcCAGTA GTTTWTACAT GTTCACGGGT C.GTTCTGCT
1-4049    CGGTCCCtGA AAGGCCAgTA GTTTWTACAT GTTCACGGGT C.GTTCTGCT
1-4050    CGGTCCCtRA AAgGcCAGTA GTTTWTACAT GTTCACGGGT C.GTTCTGCT
1-2068    CGGTCcCCgA AAGGCCAgTA GTTTATACAT GtTCACGGGT C.GTTCTGCT
1-3059    CGGTCcCCGA AAGgCcAgTA GTTTWtACAT GTtCACGGGt C.GtTCTGCT
1-4031    CGGTCcCYGA AARGccAGTA GTTTWTACAT GTTCACGGGT C.GTTCTGCT
1-4038    CGGTCCcCGA AAGGcCAGTA GTTTWTACAT GTTCACGGGT C.GTTCTGCT
1-4041    CGGTCCCCGA AAGGCcAGTA GTTTWTACAT GTTCACGGGT C.GTTCTGCT
1-4047    CGGTCCCYga AaGGCcAgTA GTTTWTACAT GTTCACGGGT C.GTTCTgCT
1-5094    CGGTCCccgA AAgGCCAGTA GTTTwTACAT GTTCACGGGT C.GTTCTGCT
1-4037    CGGTCcCtRA AABGcCAGTA GTTTWTACAT GTTCACGGGT C.GTTCTGCT
1-3060    CGGTCCCcGA AAGGCcAGTA GTTTWTACAT GTTCACGGGt c.gTTCTGCT
1-4032    CGGTCcCtGA AARGcCAGTA GTTTWTACAT GTTCACGGGt C.GTTCTGCT
1-4046    CGGTCCCYRA AAGGCCAGTA GTTTaTACAT GTTCACGGGT C.GTTCTGCT
1-4048    CGGTCCCtGA AAgGcCAGTA GTTTWTACAT GTTCACGGGT C.GTTCTGCT
1-3058    CGgTCccCGA aAGGCcAGta GTtTWTACAT G.TCACgGgt C.GTtCTGCT
1-4044    CGGTcCCCGa AAgGcCAGTA GTTTWTACAT GTtCACGGGt C.GTTCTGCT
1-5076    CGGtCCcCgA AAGGcCAGTA GTTTWTACAT GTTCACGGGT C.GTTCTGCT
1-2066    CGGTCcCtGA AAGGcCAGTA GTTTWTACAT GTTCACGGGT c.GTTCTGCT
1-5097    CGGTCCCCGA AAGGCCAGTA GTTTWTACAT GTTCACGGGT C.GTTCTGCT
1-2062    CGGtCCCygA AAGGCCAgTA GTTTWTACAT GTTCACGGGt C.GTTCTGCT
```

FIG. 6 (Continued)

```
1-3020   CGGTCCcCGA AAGGCcAGTA GTTTWTACAT GTTCACGGGT C.GTTCTGCT
1-2064   CGGTCcCCGA AAGGCCAgTA GTTTWTACAT GTTCACGGGT C.GTTCTGCT
1-2102   CGGTCCCCGa AAGGCCAgTA GTTTTTACAT GTTCrCGGGt C.GTTCTGCT
1-3057   CGGTCcCCGA AAgGcCAGTA GTTTWTACAT GTTCACgGGT C.GTTCTGCT
1-2065   CGGTCCcyGA AAgGcCAGTa GTTTWTACAT GTTCACGGGt C.GTTCTGCT
1-2067   CGGTCCCCGA AAGGCCAGTA GTTTWTACAT GTTCACGGGT C.GTTCTGCT
1-4034   CGGTCcCCGA AASGcCAGTA GTTTaTACAT GTTCACGGGT C.GTTCTGCT
1-2072   CGGTCCCCGA AAGGCcCAgTA GTTTWTACAT GTTCACGGGt C.GTTCTGCT
1-5095   CGGTCCCCGA AAGGCcCAGTA GTTTWTACAT GTTCACGGGT C.GTTCTGCT
1-2111   CGGTCCCCGA AAGGCCAGTA GTTTwTACAT GTTCACgGGT C.GTTCTGCT
1-3015   CGGTCCCCGA AAGGCCAGTA GTTT.WTACA TGTCACGGGT C.GTTCTGCT
1-3018   CGGTCcCCGA AAGGCcAGTG TTTW.TACAT GTTCACGGGT c.GTTCTGCT
1-2100   CgGTCcCCGA aARGcCAGTA GTTTWTACAT GTTCACGGGT C.GTTCTGCT
1-2104   CGGTCcCCGA AAgGcCAGtA GTTTWTACAT GTTCACGgGt C.GTTCTGCT
1-5075   CGGtCcCCGA AAGGCCAGTA GTTTWTACAT GTTCACGGGT C.GTTCTGCT
1-5096   CgGTCCCCGA AAGGCCAGTA GTTTWTACAT GTTCACGGGT C.GTTCTGCT
1-5077   CGGTCCcCGA AAGGCcAGTA GTTTWTACAT GTTCACgGGT C.GTTCTGCT
1-5073   CGGtCCcCgA AaGGCCaGTA GTTTWTACAT GTTCACGGGt C.GTTCTGCt
1-3019   CGGTCCC.gA AAGGCCAGTA GTTTWTACAT GTTCACGGGt C.GTTCTGCT
1-4039   CGGTCCcCgA AAKGcCAGTA GTTTwTACAT GTtCACGGGT CGGTTCTGCT
1-3056   cGgTCcCCgA aAgGCcAGta GTtTwTACAT GTtCACGGGT C.GTTCTGCT
1-2071   CGGTcCCCGa AAgGcCAgTA gTTTWTAcAT GTTCaCGGGG TCGTTCTGCT
1-2101   CGGTCCCCGA AARGcCAgTA GTTTWTACAT GTTCACGGGT C.GTTCTGcT 251                                                 300
1-6053   ATGCAGG.GT TCGACAATGA TCCtH..CGC AGGTTCACcc TACGGAAACc
1-6055   ATGcaGG.GT TCGAcAATGA TCCnn..CGC AGgTTcacC. .TACgGAAcC
1-6054   ATGCAGG.GT TCGAcAATGA TCCVN..cGC AGGTTcACC. tACGGAAACC
1-6052   ATGcaGG.GT tCGaCaaTGA tCCtW..CGC aGGtTcacCt aCGG...aAC
1-1105   ATGCAGGA.T TcGAcAATG. ...at.ccgc aggttcacct acggaaacct
1-5074   ATGCAGGa.T Tcgacaatga tc.nn.ccgc aggttcacct acggaaacct
1-3017   ATGcAGga.T tCGAc.AtgA TcCWw.CCGC aGGttCACct aCGGAaACCT
1-4042   ATGCAGGA.T TCGACAATGA TCCTT.CCGC AGGTTCACCT ACGGaAACCT
1-3016   ATGCAGGa.T TcGAcAaTga TCCnn.CCGC AGgttCaCCt acGGaAaCcT
1-2070   ATGcaGGa.t TCgACAATGA T.CTt.Ccgc AGCCTtCACCt AcgGaAACCT
1-3061   ATGcaGGa.T tCGacAaTga tcnnn.ncgc aggttcacct acggaaacct
1-1107   AtGcaGGa.T TCGACAATGA tCnnn.nCgC AGgTtcaCCw k.gGAAAcCt
1-4043   ATGCAGGA.T TCGACAatGA TCnnn.CCGC AgGTTCACCT a.CGAAaCCT
1-4035   ATGCAGGA.T TcGACAATGA TCCtt.CCGC aGGtTCACCT ACGGaAACCT
1-4049   ATGCAGGA.T TCGACAATGA TCCTT.CCGC AGGTTCACCT ACGGaAACCt
1-4050   ATGCAGGA.T TCGACAATGA TCCTT.CCGC AGGTTCACCT ACGGaAACCt
1-2068   ATGCAGGA.T TCgaCAATGA TCCTt.CCGC AGGtTYACCT ACGGaAACCt
1-3059   ATGCAGGA.T TCGAcAATGA TCCtt.CCSC AGGttCaCCT ACgGaAAcCt
1-4031   ATGcAGGA.T TCGACAATGA tCCtt.cCGC AGGtTCACCT ACGGaAaCct
1-4038   ATGCAGGA.T TCGACAATGA TCCTT.CCGC AGGtTCACCT aCGGaAACCT
1-4041   ATGCAGGA.T TCGACAATGA TCCwt.CCGC aGGtTCACCT ACGGaAACCT
1-4047   aTGCAgGA.T TCGaCAaTGA TCCtt.CCGC aGGTtcaCCT ACGGaAACCt
1-5094   ATGCAGGA.T TCGACAATGA TCCTt.CCGC AGGtTCACCT ACGGaAACCT
1-4037   ATGCAGGA.T TCGACAATGA TCCtT.CCGC AGGTTCACCT ACGGAaACCT
1-3060   ATGcAGGa.T TcGACAATGa TCCtt.CCGC AGGTTCACCT ACGGaAACCT
1-4032   ATGCAGGA.T TcGACAATgA TCnnn.ccGC a.GtTCACCT ACGGAAaCcT
1-4046   ATGCAGGA.T TCGACAATGA TCnnn.ccgC A.GTTCACCT ACGGAAACcT
1-4048   ATGCAGGA.T TCGACAATgA TCCTt.CCGC A.GTTCACCt ACGG.AAcCt
1-3058   ATGcAGGa.T tcgAcAaTga Tccnn.CcGc a.GTtCACcT AcGgaAACcT
1-4044   ATGCAgGA.T TCGACAATgA TcKYt.CCGC A.GttCACCt ACGGaAACct
```

FIG. 6 (Continued)

```
1-5076  ATGCAgGA.T  TCGACaATGA  TCnnn.CCGC  A.GTTCACCT  ACgGAAACCT
1-2066  ATGCAGGa.T  TCGACAatGA  Tcnnn.nCgC  A.GTTCaCct  ACgGAAAccT
1-5097  ATGCAGGA.T  TCGACAATGA  TCCTT.CCGC  A.GTTCACCT  ACGGAAACCT
1-2062  ATGCAgga.T  TcGACAATGA  TCnnn.CCGC  aGGtTCACCt  ACGGAAaacC
1-3020  ATGcaGGA.T  TCGACAATGA  TCCtt.CCGC  aGGTTCACCT  ACCGGaAACC
1-2064  ATGCAGGA.T  TCGACAATGA  TCCTT.CCGC  AGGTTCACCT  ACGGAAACCT
1-2102  AtGCAgGA.T  TCGACAATGA  tnnnn.ccgc  aggttcacct  acggaaacct
1-3057  ATGCAGGA.T  TCGACAATGA  TCCTT.CCGC  AGGTtCACCT  ACGGAAACcT
1-2065  ATGCAGGa.T  TCGACAATGA  TCCTT.CCGC  AGGtTCACCT  ACGGaAACCT
1-2067  ATGCAGGA.T  TCGACAATGA  TCCTT.CCGC  AGGTTCACCT  ACGGAAAcCt
1-4034  ATGcaGGA.T  TCGaCAATGA  TCCtT.CCGC  AGGTTCACCT  ACGGaAaCCT
1-2072  AtGCAgGA.T  TCgACAAtgA  tCcKT.CcGC  AgGTTCacCt  ACgGAAaCCT
1-5095  ATGCAGGA.T  TCGACAATGA  TCCtt.CCGC  AGGTTCACCT  ACGGaAACCT
1-2111  ATGCAGGA.T  TCGACAATGA  TCnnT.CCGC  AGGTTCACCT  ACGGAAACCT
1-3015  ATGCAGGA.T  TCGACAATGA  TCCTT.CCGC  AGGTTCACCT  ACGGaAACCT
1-3018  AtGcaGGA.T  TcgacAAtGA  tCdnK.cCGc  aGGtTcaCCt  ACGGaAaCCT
1-2100  ATGCAGGa.T  TcgacAATGA  tcnnn.ccgc  aggttc.ccn  nnggaaacct
1-2104  AtGCAgGa.t  TCGacAaTgA  TCnnT.CCGC  aGGTTCAcCt  ACGGaAaCcT
1-5075  ATGCaGGa.T  TCgacAATga  tcnnn.ncgc  a.gttcaccw  ..bggaaact
1-5096  ATGCAGGA.T  TCGACAATGA  TCCTT.CCGC  A.GtTCACCT  ACGGaAACcT
1-5077  ATGCAGGATT  TCGAcAAtGA  tnnnn.ccgc  aggttcacct  atcggaaacc
1-5073  ATGCaGGA.T  TCGacAaTGA  TcCKY.cCGC  AGGttcaCCT  ACgGAAaCCT
1-3019  ATGCAGgm.t  TcgACAATGA  TCCtTCCCGC  AGGTtCACCt  ACGGAAaCTT
1-4039  ATGCAGGA.T  TCGACAATGA  TCCTt.cCGC  AGGTTCACCt  ACGGAAaCCT
1-3056  ATgcAGga.T  tCGACAaTgA  tcCtt.CcGC  AGgTtCA.CT  AcGgaaAcCT
1-2071  ATGCaGGA.T  TcGAcaatga  tcnnnccgca  ggttcaacct  acggaaacct
1-2101  ATGCAGGA.T  TCGaCAATAG  atcnnnccgc  aagttcacct  abggaaacct 301         317
1-6053  TTGT.ACGAC  TtTACt~
1-6055  TTGT.acgAc  TTTAct~
1-6054  TtGT.AcGAC  TTTAct~
1-6052  TtgT.aCGaC  TTTAct~
1-1105  tgttacgact  tttact~
1-5074  tgttacgact  tttact~
1-3017  tGT..ACgac  tTTAct~
1-4042  TGT..ACGAC  tttact~
1-3016  TGT..AcgaC  TTTACT~
1-2070  tGT..ACGAC  ttttact
1-3061  tgt..acgac  t~~~~~~
1-1107  tG.T.AcgAc  tTtTAc~
1-4043  Tg.T.aCGAC  TTTaCT~
1-4035  TG.T.ACGAC  TttTAct~
1-4049  TG.T.ACgAc  TTTtact
1-4050  TG.T.ACGAC  TTTTACt
1-2068  TG.T.ACgaC  TTTact~
1-3059  Tg.T.AcgAC  TTTACt~
1-4031  tG.T.ACGAC  tTtACT~
1-4038  Tg.T.ACGAc  TTTACt~
1-4041  TG.T.ACGAC  TTTACt~
1-4047  tG.T.ACGAC  TTTAct~
1-5094  TG.T.ACGAC  TTTACt~
1-4037  tg.T.ACGAC  TtTACt~
1-3060  tG.T.ACgAc  TTTAC~~
1-4032  Tg.T.AcgAc  TtTAct~
```

FIG. 6 (Continued)

```
1-4046   Tg.T.ACGAC TTTacT~
1-4048   TG.T.ACGAc TTTACT~
1-3058   TG.T.AcGac TtTacT~
1-4044   tGTT.ACGAC TTT~~~~
1-5076   TGTt.ACGAc tTTTAct
1-2066   TGTt.ACgaC TTtTAct
1-5097   TGTT.ACGAc wTTTACT
1-2062   TTGT.ACGaC TTTTaCt
1-3020   tTGT.ACGAC TTTTAct
1-2064   TGTT.ACGAC TTTACt~
1-2102   tgtt.acgac ~~~~~~~
1-3057   tgTT.ACGAC TTt~~~~
1-2065   TGTT.ACGAC TTTaCT~
1-2067   Tgtt.acgAc tTTTAct
1-4034   TGtT.ACgaC TTtTAct
1-2072   TgtT.acGAC cTTTACT
1-5095   TGTT.ACGAC TTTAACt
1-2111   TGTT.ACCGA CCTT~~~
1-3015   TGTt.ACGAC TtTACt~
1-3018   TGTA.ACgaC TTTacT~
1-2100   tg.taacgac ttttact
1-2104   TgTWAACGAC TTttact
1-5075   tgttacgact tttact~
1-5096   TGTACAGACT TTAcTC~
1-5077   ttgttacgac ttttact
1-5073   tGTACgCtTT TAct~~~
1-3019   GCT..ACGAC TTTaCt~
1-4039   TGT..ACGAC TtTACT~
1-3056   tgT..AcgAc TTTACt~
1-2071   tgtt.acgac tttact~
1-2101   tgttaacgac ttttact
```

FIG. 6 (Continued)

1,2: *E. angustifolia*
3,4: *E. atrorubens*
5: *E. pallida*
6,7: *E. purpurea*
8: *E. purpurea* (dried root powder)

US 7,811,766 B2

GENETIC IDENTIFICATION AND VALIDATION OF *ECHINACEA* SPECIES

RELATED APPLICATIONS

This application claims priority of U.S. Provisional Application No. 60/908,586, filed Mar. 28, 2007, the content of which is hereby incorporated into this application by reference.

SEQUENCE LISTING

This application is accompanied by a sequence listing that accurately reproduces the sequences described herein.

BACKGROUND

1. Field of the Invention

The present disclosure pertains to methods for identification of plant species using molecular genetic tools. More particularly, the disclosure relates to validation of *Echinacea* species through DNA polymerase chain reaction (PCR) using primers designed based on their information content.

2. Description of Related Art

The use of dietary supplements, particularly vitamins and botanicals, have become very popular in the United States and Europe. A recent survey conducted by the FDA found that 16 million Americans use botanical supplements. The industry has consistently grown at a rate of approximately 25% annually since 1990. Supplements containing the Purple Coneflower, *Echinacea purpurea* and other related species, is one of the top selling products. A survey published in USA Today indicated that 19% of adult Americans have used *Echinacea* for the treatment of colds and flu symptoms. The plant contains substances that have been shown to non-specifically stimulate the immune system in animals and man (Stimpel et al. 1984; Roesler et al. 1991a, 199b). Bioactive high-molecular-weight polysaccharides are believed to be involved in a stimulation of lymphocytic macrophages and B cells with the production of various cytokines (e.g. interleukins, tumor necrosis factor and interferons). The response has been measured in-vivo and verified in clinical studies (Braunig et al 1992; Schoneberger et al. 1992). These plant used in its typical dosage forms has also been shown to non-toxic with no measurable side effects or known contraindications (Mengs et al. 1991).

The North American genus *Echinacea* consists of nine species and multiple varieties and has a distribution centering on Arkansas, Oklahoma, Missouri and Kansas. While the species are relatively distinct from one another, specific differences are narrowly defined. All taxa will hybridize when brought together and considerable natural hybridization occurs (McGregor 1968). *E. angustifolia* and *E. atrorubens*, which show geographic introgression, exhibit considerable overlap in stem and petiole structures. Hybrids of *E. simulata* and *E. sanguinea* appear to be very similar to the Arkansas race of *E. pallida*, and *E. simulata* has in the past been considered a variety of *E. pallida*. Further studies revealed differences in pollen size and morphology and that *pallida* was polyploid, and those natural hybrids were triploid and sterile. Because of hybridization, similarities between species and overlapping ranges, the identification of *Echinacea* species based on morphological characteristics alone is a complex process that is prone to ambiguity.

The currently practiced methods for identification of botanical species from processed plant materials (dried roots, stems, leaves, flower and seed) involve the chemical identification of chromatographic profiles of plant secondary products. These chromatographic techniques include thin-layer chromatography (TLC) and high performance liquid chromatography (HPLC). The identification of a plant species is accomplished by comparison of chemical constituent profiles with chemical standard mixtures derived from extracts of a voucher plant specimen. Confirmations are often made by microscopic evaluation of the processed plant material. The results obtained from such analysis are subject error and misinterpretation because many plant secondary products are common within families and genera, and their natural variability can be influenced by growth cycle and habitat.

Public safety and product efficacy demand uniform state-of-the-art quality assurance programs. The Food & Drug Administration has a mandate to begin regulation of the dietary supplement industry for quality assurance and good manufacturing practices (US Code, 63 Fed. Reg. 23624). With the implementation of regulations to ensure quality control of product manufacture of phytomedicinals (21 CFR 201.128, Food & Drug Cosmetic Act), species certification is likely to be required of all botanical raw materials. Even if not required by the FDA, such certification increases consumer confidence and provides a competitive market advantage for producers of the certified product. It is also conceivable that, certification may become contractually mandated by international importers of phytomedicinals or by traders in commodity futures markets.

Molecular genetic analysis of highly conserved genes have been used in species identification because distinct genetic sequences are found in different species and in some instances individuals within the same species. These profiles can be determined with great precision and when properly applied are reproducible, rapid and scalable to large numbers of specimens. In addition to DNA sequence analysis, various DNA-based methods have been used to identify differences among individuals, populations and plant or animal species. In plant taxonomy, the techniques of RFLP (Restriction Fragment Length Polymorphism) and AFLP (Amplified Fragment Length Polymorphisms) have been used to characterize genetic differences between species and their sub-populations. Both procedures generate an array of DNA fragments of varying lengths is generated by these procedures that are unique for a given individual organism. The RFLP method is does not provide optimal discrimination of species (Hollis et al. 1999), requires highly purified DNA, and is not easily scaled to large numbers of specimens and can give erroneous results due to epigenetic differences between species (Jupe and Zimmer 1990). AFLP has been used to characterize the taxonomy of the genus of *Echinacea* (Baum et al. 2002). This technique, however, can be difficult to reproduce in different laboratories. This may be due to the fact that the AFLPs are derived from highly repetitive sequences that are not stable in plant genomes (Reamon-Buttner S M et al. 1999).

SUMMARY

It is hereby disclosed a genetic method for the identification of each of the nine species of commercially-produced *Echinacea*. It is an objective of this invention to provide a reliable method to certify the purity of the plant material distributed in the US and overseas. Accurate identification of each species would detect adulteration with other species and be impervious to adulteration with active chemical constituents. It is another goal of this invention to develop genetic technology that will be commercialized into both products (kits) and analytical services for distributors of botanical products, neutraceutical manufacturers and agricultural producers. The use of DNA sequence analysis to analyze ingredients in herbal supplements for the identification of species represent a significant improvement over existing methodology in *Echinacea* taxonomy. Existing HPLC methods for evaluating *Echinacea* extracts cost $200-300 per specimen and are not as accurate as the methodology present disclosed. In addition to its accuracy, the methods disclosed here are also simple to perform with a cost similar to or less than HPLC. High throughput (multiwell plate) testing may be performed at a cost less than current HPLC methods and provide more information in each test. In manufacturing a typical neutraceutical product, the cost of quality control of raw materials is estimated to be approximately 1% of product sales. If this DNA analytical procedure is applied to 20% of QC costs for all botanical supplement products, then the potential for sales of this analytical service is ~$10 million annual sales in today's market.

The methods hereby disclosed are based upon the technology disclosed in U.S. Pat. No. 5,849,492 (the '492 patent), which describes DNA amplification and sequencing assay (omnibus PCR) to accurately identify a wide spectrum of organisms in vitro without culturing or growing the organisms. The '492 patent also describes primer sequences for 16S rDNA and 28S rDNA for identification of prokaryotic and eukaryotic organisms, respectively. The teachings of the '492 patent are hereby expressly incorporated into this disclosure by reference.

The sequences of ribosomal RNA molecules have been used to identify genetic differences between bacterial species (Woese, 1987). Other DNA technologies, such as Amplified Restriction Fragment Polymorphism analysis, have produced ambiguous results when used to identify species (See, e.g., Binns et al. 2002; Kim et al 2004; Bobowski et al., 1999). The present work is aimed at developing a method to use DNA from the coding sequences of ribosomal RNA to distinguish different *Echinacea* species. Briefly, ribosomal nucleotide sequences that are either published or unpublished are used to investigate their suitability in distinguishing multiple varieties of five different *Echinacea* species and *Parthenium integrifolium*, a reported adulterant in *Echinacea* products (Bauer, 1998b). These studies may also reveal other intraspecies genetic variation that can distinguish different varieties.

Thus, it is disclosed herein a number of oligonucleotide pairs for amplification of ribosomal DNA from a plant material, including primer set 1, primer set 2, primer set 3, and primer set 4, the sequences of which are detailed in the Examples. It is also disclosed methods for identifying a plant species or for validating a plant material based on the primary structure of the DNA contained within the plant species or the plant material, said method comprising amplification of a segment of the internal transcribed spacer region of the ribosomal DNA of said plant species. In one aspect, the primer pair used for the amplification is *Echinacea* specific, or in other words, the primers specifically amplify DNA from *Echinacea* species but do not amplify DNA from *Parthenium* species. In another aspect, the primer pair used for the amplification is *Parthenium* specific, namely, they specifically amplify DNA from *Parthenium* species but do not amplify DNA from *Echinacea* species. Preferably, the primer pair used for the amplification is selected from the group consisting of primer set 1, primer set 2, primer set 3, and primer set 4.

It is also disclosed a method for determining the existence of an organism or its derivatives in a material. For purpose of this disclosure, derivatives of an organism means a material that is derived from any parts or tissues of the organism. In one embodiment, the method may include the following steps: (1) a first DNA amplification may be performed to amplify a segment on a ribosomal DNA, wherein a first primer pair is used as PCR primer. DNA from at least one species belonging to the same genus as said organism may be used as template for the first DNA amplification; (2) the resultant PCR product resulting from the first amplification may be sequenced; and (3) a second DNA amplification may be performed using as PCR primer a second primer pair and using as template DNA prepared from said material.

In one aspect, the selection of the first primer pair may include the steps of: (a) searching for a divergent segment of the DNA from said at least one species with low average information content determined quantitatively surrounded by two conserved segments of said DNA with high average information content determined quantitatively; and (b) designing the first primer pair for PCR amplification of said divergent segment by constructing a sequence logo for said DNA such that said primers contain a set of sequences present in said sequence logo that encompass the nucleotide variability of said conserved segments, said primer pair being able to anneal to said conserved segments for amplication of said divergent segment. The calculation of average information content and the construction of logo may be performed based on methods taught in the '492 patent.

The second primer pair may be selected by first searching the sequences obtained from step (2) above for at least one segment of DNA with significant interspecies variations; and then by designing the second primer pair for DNA amplification, wherein said second primer pair comprises at least one interspecies variation. More preferably, the second primer pair includes at least one interspecies variation such that it only amplifies DNA from certain species, but not others. Most preferably, the second primer pairs are selected such that one primer pair would amplify most species of either the *Echinacea* or *Parthenium* genus, but not both.

In one embodiment, the template for the amplification is DNA prepared from a target sample, such as target sample obtained from harvest of a previous growing season, which typically means a growing season at least 6 months before. Thus, the target samples may be stored for 6 months, or even longer.

In another aspect of the present disclosure, the target sample may contain specimen from more than one species, such as, for example, from at least two species selected from the group consisting of *Echinacea*, *Parthineum* and *Rudbeckia*. Preferably, the target sample contains specimen from *Echinacea* and *Parthineum*.

BRIEF DESCRIPTION OF THE DRAWINGS

FIG. 1 shows multiple alignment of published ribosomal ITS1 sequences from several *Echinacea* species, *E. paradoxa* (SEQ ID No. 1), *E. simulata* (SEQ ID No. 2), *E. pallida* (SEQ ID No. 3), *E. purpurea* (SEQ ID No. 4), *E. tenesseensis* (SEQ ID No. 5), *E. atrorubens* (SEQ ID No. 6).

FIG. 3 is a DNA sequence alignment of a segment of the ITS1 region obtained by amplification and sequencing of the ITS1 regions from genomic DNA extracted from *Echinacea* specimens collected as described in this disclosure, with the 11 sequences shown designated as SEQ ID Nos. 7-17, respectively.

FIG. 4 is a DNA sequence alignment of a segment of the ITS1 region obtained by amplification and sequencing of the ITS1 regions from genomic DNA extracted from *Parthenium* specimens collected as described in this disclosure, with the 4 sequences shown designated as SEQ ID Nos. 18-21, respectively.

FIG. 5 is a DNA sequence alignment of a segment of the ITS2 region obtained by amplification and sequencing of the ITS2 regions from genomic DNA extracted from various *E. angustifolia* specimens collected as described in this disclosure, with the 3 sequences shown designated as SEQ ID Nos. 22-24, respectively.

FIG. 6 is a DNA sequence alignment of a segment of the ITS2 region obtained by amplification and sequencing of the ITS1 regions from genomic DNA extracted from *Echinacea* and *Parthenium* specimens collected as described in this disclosure, with the 57 sequences shown designated as SEQ ID Nos. 25-81, respectively.

DETAILED DESCRIPTION

Figure 2:
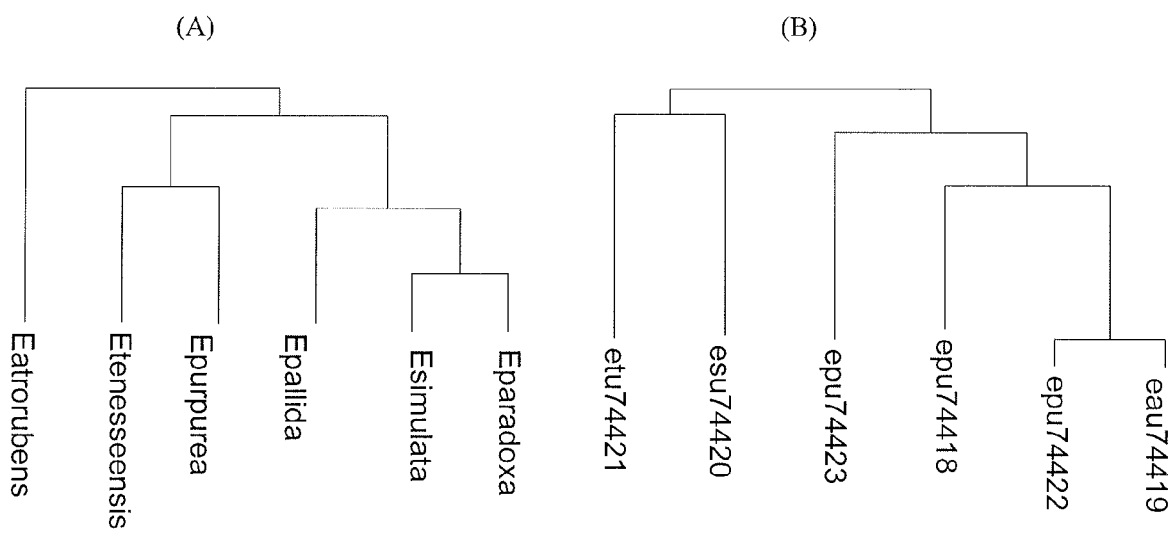
FIG. 2 shows neighbor-joining dendrograms depicting phylogenetic relationships of *Echinacea* species based on corresponding sequence differences in the ribosomal intergenic spacer region. (A) ITS1 (B) ITS2.

Polymerase chain reaction (PCR) used in this disclosure may be performed as described by Mullis and Faloona (1987) and any subsequent modification to the methodology originally invented by Mullis. All temperatures stated in this disclosure are centigrade unless otherwise specified.

Since almost all organisms employ ribosomes to synthesize proteins, ribosomal subunits have been structurally and functionally conserved throughout the eons. As a result, ribosomal RNAs from widely differing species may differ in only a small number of nucleotides. These limited sequence variations may be used to characterize the evolutionary or phylogenetic relationships between the organisms and to identify a specific organism. Briefly, information (in bits) may be used to precisely quantify both the similarities and divergence among 16S gene sequences, because information measures the number of choices between two equally likely possibilities (Schneider et al., *J. Mol. Biol.* 188: 415-431, 1986). Variable positions in a multiply aligned set of 16S rDNA sequences approach zero bits and homologous or highly conserved sequences have nearly two bits in a sequence logo (Stephens & Schneider, *Nucl. Acids Res.* 18: 6097-6100, 1990), which displays the average information content ($R_{sequence}$) and frequencies of each nucleotide at each position.

The average information in bits of a related set of sequences, $R_{sequence}$, represents the total sequence conservation:

$$R_{sequence} = 2 - \left[ -\sum_{b=a}^{t} f(b, l) \log 2 f(b, l) + e(n(l)) \right] \quad (I)$$

f(b,l) is the frequency of each base b at position l, e(n(l)) is a correction for the small sample size n at position l.

A sequence logo may then be constructed based on the $R_{sequence}$ to locate segments consisting of sequences with low information content flanked on either side by sequences with high information content.

Both the similarities and differences between organisms may be used to obtain the identity of these organisms. Morphological and biochemical properties have been used to differentiate among different organisms. However, these methods can be time consuming and can be inaccurate. False results may be generated if the culturing condition used is less than optimal, and thus the assay fails to identify the organism that is present in a specimen. According to the present disclosure, nucleic acid sequences of homologous genes in different species may reveal the identity of infectious agents. The frequency and arrangement of nucleotide differences indicate the degree to which two organisms have diverged from a common ancestor. In a preferred embodiment, the sequences of ribosomal DNA may be used to identify genetic differences between different species.

In order to ensure that the widest spectrum of organisms may be identified, it is desirable to apply the information theory-based sequence analysis to a greatest possible number of species to select for sequences in the homologous 16S ribosomal RNA genes (16S rDNA) for DNA amplification. In one embodiment, full length 16S rDNA sequences from a set of bacterial species (2184 organisms obtained from Genbank v88; National Library of Medicine) having the broadest possible taxonomic distribution are used to design amplification experiments (Saiki et al., *Science* 230: 1350-1354, 1985).

The total information content at each position may be used as the basis for selecting phylogenetically-informative regions flanked by segments about 18 bp or more showing sufficient sequence conservation to be used as primers for the PCR amplification reaction. The ratio of the number of bits of each nucleotide at each position to the total number of bits at that site may determine the proportion of a particular nucleotide at degenerate sites in the oligonucleotide primer. A ratio of 0.001 may be taken as the minimum proportion required to include this nucleotide in a degenerate site (see below). Otherwise, the primer may be designed to be homogeneous at that position.

A sequence logo may be used to locate several segments consisting of sequences with low information (>100 nucleotides, average $R_{sequence}=0.2$) content flanked on either side by sequences with high information content and tested experimentally (Rogan et al., 1995; Tooley P W, Salvo J J, Schneider T D, Rogan P K: Phylogenetic inference using information theory-based PCR amplification. J Phytopathology, 146(8-9): 427-430, 1998; U.S. Pat. No. 5,849,492). Alternatively, alignment and visual inspection of sequences from different species may be employed to select a set of primers suitable for PCR amplification of segments of DNA from these species. An ideal set of primers preferably anneals to regions that show relatively high sequence similarity across species, and also preferably flanks a segment of DNA that demonstrates high sequence variation among species.

The PCR product may be purified using a number of established methods for DNA purification. Preferably, the PCR product is purified using magnetic separation, or gel purification. Magnetic separation may have a higher yield of recovered PCR product than gel purification. At least one primer may be biotinylated if magnetic separation of PCR product is to be used. Although gel purification produces relatively lower yield and requires higher amount of the amplified DNA, gel purification has proven helpful in some instances in reducing the problem of concatomers of PCR products that may cause difficulty in obtaining clean sequence data. One potential drawback for gel purification is that it may not be as conducive to automation as magnetic separation. Magnetic separation is the preferred method for purifying the PCR products.

The purified PCR products may be characterized by sequencing or other molecular tools. Sequencing methods such as the dideoxy method or the chemical method may be used Sanger F, Nicklen S, Coulson A R, "DNA sequencing with chain-terminating inhibitors." Proc Natl Acad Sci USA. 1977 74 (12):5463-7; Maxam A M and Gilbert W, "Sequencing end-labeled DNA with base-specific chemical cleavages." Methods Enzymol. 1980; 65(1):499-560. The sequences may be read from a film exposed to the sequencing gel or may be obtained using an automated sequencing machine. Other molecular tools such as mass spectrometry or other structural analysis tools capable of discerning the difference in primary sequence may also be used to characterize the PCR products. Some of these tools for molecular characterization of DNA have been summarized in a review article by V. K. Khanna, "Existing and emerging detection technologies for DNA (Deoxyribonucleic Acid) finger printing, sequencing, bio- and analytical chips: A multidisciplinary development unifying molecular biology, chemical and electronics engineering" Biotechnology Advances, 2007, 25:85-98, which is hereby incorporated by reference.

If conventional DNA sequencing is used, when the sequencing run is finished, DNA sequence analysis software, such as Visible Genetics OpenGene, may be used to align and base call the electropherogram. Preferably, the sequence data are manually checked and edited to obtain as clean and accurate a sequence as possible prior to sequence analysis. In some situations, the electropherogram may need to be manually aligned and/or base called because of the limitations of the software.

Using the PCR and sequencing methodology described above, there may be instances where the sequence is not readable because there are multiple peaks at several locations in the sequence. This problem typically arises when more than one organisms are present in the same sample. To eliminate this problem, a constant denaturing gel electrophoresis (CDGE) protocol may be used, which allows DNA to be separated on the basis of sequence composition and duplex stability in a vertical polyacrylamide gel.

Phylogenetic relationships have been inferred from nucleotide sequence variations in the internal transcribed spacer regions (ITS) of 18S-25S nuclear ribosomal DNA genes of angiosperms. The taxonomies from ITS data, which are generally concordant with phylogenies derived from chloroplast and other nuclear gene sequences, have resulted in some reclassification of angiosperms at the ordinal level (Soltis and Soltis 2000). With few exceptions (e.g. Francisco-Ortega et al. 1999), different angiosperm species are resolved by ITS sequence analysis, though the tree topologies can differ from those based on vegetative and floral morphology (e.g. Aceto et al. 1999). ITS-based taxonomies are congruent with other nuclear gene phylogenies (e.g. Emshwiller and Doyle 1999), but nevertheless, can display higher bootstrap values than those based on chloroplast genes (e.g. Gielly et al. 1996), due to higher levels of interspecies sequence divergence in the ITS region.

The ribosomal intergenic spacer sequences (ITS) can be used to differentiate among several *Echinacea* species. Two different sequence regions, known as ITS1 and ITS2, have been shown to exhibit the largest amount of interspecies variability. Six sequences of the ITS1 region from different *Echinacea* species have been reported in GenBank (Accession nos. U73148, U73149, U73150, U73151, U73152, U73153). These sequences have not been peer reviewed but may be used to demonstrate their suitability for use in differentiating between different *Echinacea* species.

As shown in FIG. 1, variations in nucleotide sequence may be found in each ITS1 DNA sequence from different *Echinacea* species. Bolded positions in the alignment illustrate sites where these species may be distinguished based on sequence variations. For instance, *E. tenesseensis* lacks cytosine at position 10 in the multiple alignment shown in FIG. 1, whereas it is present in the other species. Similarly, *E. atrorubens* differs at positions 42 and 50 of the alignment. *E. purpurea* and *E. tenesseensis* both contain adenosine at position 66, whereas guanosine is present in the other species. Only *E. paradoxa* and *E. simulata* lack guanosine at position 162, and may be distinguished from each other based on an extra adenosine in *E. simulata* at position 220 in the multiple alignment shown in FIG. 1.

Certain intraspecies variations based on ITS polymorphism may exist in species which have a high frequency of introgression during domestication or polyploidization (Jobst et al. 1998). However, ITS intraspecies variation does not appear to be common in undomesticated, non-hybridized species (Ainouche and Bayer 1997). For those species of *Echinacea* that appear to result from interspecies hybridization (e.g. *E. simulata*), phylogenetic relationships may be inferred from the multiple sequence differences present in the ITS regions of the interspecies hybridization progenies when compared to the same regions of the parental species.

The sequence of *Echinacea* ITS2 shows fewer variable sites between species than ITS1. The ITS1 and ITS2 sequences may be useful in constructing phylogenetic trees that depict the taxonomic relationships between the organisms (FIG. 2). The alignment on which these trees is based is anchored by a highly conserved sequence, GGCRY-$(N_{4-7})$-$(GY)_2$CAAGGAA, located in ITS1 (Liu and Schardl 1994). In FIG. 2, neighbor-joining dendrograms are based on distances computed with 2-parameter substitution rates, however unweighted parsimony trees produced similar topologies.

The number of publicly available ITS sequences of *Echinacea* is limited. More importantly, due to interspecies variations, it is unclear how well the published sequences of the *Echinacea* ITS regions represent *Echinacea* specimens obtained from the market. In order to develop a methodology that is suitable for identification and validation of *Echinacea* species in the market place, it is important to analyze sequences of the ITS regions using *Echinacea* specimens obtained from the market or from nature.

The samples to be tested (referred to as "target samples" in this disclosure) according to the disclosed methodology may range from fresh specimens to dried samples. These samples may be taken from roots, stems, leaves, flower or seeds of the plants. The disclosed methods are also suitable for verifying the identity of species contained in samples from previous growing seasons that have been kept in a warehouse. Typically, the samples are washed and pulverized before genomic DNA is extracted from the samples. Because the extraction process may cause damages to the integrity of the genomic DNA, DNA polymerases, such as the Klenow Fragment, may be used to repair such damages. The repairing process may fix gaps on the genomic DNA and may facilitate the subsequent PCR which uses the genomic DNA as a template.

The following examples illustrate the present invention. These examples are provided for purposes of illustration only and are not intended to be limiting. The chemicals and other ingredients are presented as typical components or reactants, and various modification may be derived in view of the foregoing disclosure within the scope of the invention. It is also recognized that although the examples below are given in the context of analyzing *Echinacea* samples, specimens from other plants may be analyzed with the disclosed methodology with or without modification. Nucleotide sequences disclosed herein may be presented as upper or lower case letters, both referring to the same nucleotide as is conventional in the art.

Example 1

Collection and Preparation of Samples for Nucleic Acid Analysis

More than one hundred specimens of *Echinacea* and *Parthenium* plants from across the growing range of these plants in the Midwest of the United States were collected. Table 1 is a list of specimens obtained through this endeavor. Some specimens were collected directly from the wild and kept as fresh samples, while others were dried samples that have been in storage. Genomic DNA was prepared from these specimens and DNA of the ITS regions was obtained by DNA amplification. More particularly, ITS1 primers were known to amplify the ITS genomic sequences from angiosperms and were synthesized according to Koopman et al., 1998 and Van der Stappen, et al., 1998. Each of ITS1 primer was separately modified by placing M13 and T7 sequences upstream of the sequence which is homologous to genomic DNA. Primers were also 5' biotinylated to permit magnetic capture and purification of sequencing templates. This facilitated automated sequencing of both strands of the amplification product using commercially-available Cy5- and Cy5.5-labeled universal M13 and T7 primers.

Primer selection for amplification and/or sequencing was also facilitated by use of the methodology described in U.S. Pat. No. 5,848,492. We verified that the primer sequences reported by Van der Stappen et al. 1998 And Koopman et al. 1998 demonstrated high levels of average information content. Primers and amplification products were developed first by aligning and computing the average information for 28S ribosomal RNA gene sequences of flowering plant species. Oligonucleotide primers were selected, synthesized (by Oligos Etc, Wilsonville, Oreg.), and tested using methods described in Rogan et al. 1995 and Tooley et al. 1998. The amplified products were then sequenced using primers and methods as described in FIG. 1b of Van der Stappen et al. 1998 and primers prITS2 and prITS3. Primers prITS2 and prITS3 are complementary to each other and were used in separate sequencing reactions. Their sequences are shown below:

(SEQ ID NO. 82)
prITS2: 5'-gCT gCg TTC TTC ATC gAT gC-3'

(SEQ ID NO. 83)
prITS3: 5'-gCA TCg ATg AAg AAC gCA gC-3'

The resulted sequences were compared with one another by sequence alignment. Multiple sequences from the same genus were aligned to create a multialignment of the sequences.

TABLE 1

List of Specimens Collected

| Sample ID* | Species |
|---|---|
| 3001 | *E. pallida* |
| 3002 | *E. pallida* |
| 3003 | *E. pallida* |
| 3004 | *E. pallida* |
| 3005 | *E. pallida* |
| 3006 | *E. pallida* |
| 3007 | *E. pallida* |
| 3008 | *E. pallida* |
| 3009 | *E. pallida* |
| 3010 | *E. pallida* |
| 3011 | *E. pallida* |
| 3012 | *E. pallida* |
| 3013 | *E. pallida* |
| 3014 | *E. pallida* |
| 3015 | *E. pallida* |
| 3016 | *E. pallida* |
| 3017 | *E. pallida* |
| 3018 | *E. pallida* |
| 3019 | *E. pallida* |
| 3020 | *E. pallida* |
| 4021 | *E. atrorubens* |
| 4022 | *E. atrorubens* |
| 4023 | *E. atrorubens* |
| 4024 | *E. atrorubens* |
| 4025 | *E. atrorubens* |
| 4026 | *E. atrorubens* |
| 4027 | *E. atrorubens* |
| 4028 | *E. atrorubens* |
| 4029 | *E. atrorubens* |
| 4030 | *E. atrorubens* |
| 4031 | *E. atrorubens* |
| 4032 | *E. atrorubens* |
| 4033 | *E. atrorubens* |
| 4034 | *E. atrorubens* |
| 4035 | *E. atrorubens* |
| 4036 | *E. atrorubens* |
| 4037 | *E. atrorubens* |
| 4038 | *E. atrorubens* |
| 4039 | *E. atrorubens* |
| 4040 | *E. atrorubens* |
| 4041 | *E. atrorubens* |
| 4042 | *E. atrorubens* |
| 4043 | *E. atrorubens* |
| 4044 | *E. atrorubens* |
| 4045 | *E. atrorubens* |
| 4046 | *E. atrorubens* |
| 4047 | *E. atrorubens* |
| 4048 | *E. atrorubens* |
| 4049 | *E. atrorubens* |
| 4050 | *E. atrorubens* |
| 6051 | *P. integrifolium* |
| 6052 | *P. integrifolium* |
| 6053 | *P. integrifolium* |
| 6054 | *P. integrifolium* |
| 6055 | *P. integrifolium* |
| 3056 | *E. pallida* |
| 3057 | *E. pallida* |
| 3058 | *E. pallida* |
| 3059 | *E. pallida* |
| 3060 | *E. pallida* |
| 3061 | *E. pallida* |
| 2062 | *E. angustifolia* |
| 2063 | *E. angustifolia* |
| 2064 | *E. angustifolia* |
| 2065 | *E. angustifolia* |
| 2066 | *E. angustifolia* |
| 2067 | *E. angustifolia* |
| 2068 | *E. angustifolia* |
| 2069 | *E. angustifolia* |
| 2070 | *E. angustifolia* |
| 2071 | *E. angustifolia* |
| 2072 | *E. angustifolia* |
| 5073 | *E. paradoxa* |
| 5074 | *E. paradoxa* |
| 5075 | *E. paradoxa* |

TABLE 1-continued

List of Specimens Collected

| Sample ID* | Species |
|---|---|
| 5076 | E. paradoxa |
| 5077 | E. paradoxa |
| 5078 | E. paradoxa |
| 5079 | E. paradoxa |
| 5080 | E. paradoxa |
| 5081 | E. paradoxa |
| 5082 | E. paradoxa |
| 5083 | E. paradoxa |
| 5084 | E. paradoxa |
| 5085 | E. paradoxa |
| 5086 | E. paradoxa |
| 5087 | E. paradoxa |
| 5088 | E. paradoxa |
| 5089 | E. paradoxa |
| 5090 | E. paradoxa |
| 5091 | E. paradoxa |
| 5092 | E. paradoxa |
| 5093 | E. paradoxa |
| 5094 | E. paradoxa |
| 5095 | E. paradoxa |
| 5096 | E. paradoxa |
| 5097 | E. paradoxa |
| 5098 | E. paradoxa |
| 5099 | E. paradoxa |
| 2100 | E. angustifolia |
| 2101 | E. angustifolia |
| 2102 | E. angustifolia |
| 2103 | E. angustifolia |
| 2104 | E. angustifolia |
| 1105 | E. purpurea |
| 1106 | E. purpurea |
| 1107 | E. purpurea |
| 1108 | E. purpurea |
| 1109 | E. purpurea |
| 2110 | E. angustifolia |
| 2111 | E. angustifolia |
| 2112 | E. angustifolia |
| 2113 | E. angustifolia |
| 2114 | E. angustifolia |
| 2115 | E. angustifolia |
| 2116 | E. angustifolia |
| 2117 | E. angustifolia |
| 2118 | E. angustifolia |
| 2119 | E. angustifolia |

*A prefix of "PAT," "PAT1_" or "1_" may be added before the 4-digit Sample ID in this Table without changing the identity of the sample.

FIG. 3 and FIG. 4 show the multiple alignment of sequences of the ITS1 region from *Echinacea* and *Parthenium* specimens, respectively. FIG. 5 shows the alignment of the ITS2 region from specimens from one single species, *Echinacea angustifolia*. Taken together, the data in FIGS. 3-5 and Table 1 indicate that while the DNA sequences of the ITS regions are well conserved among different species, there are significant interspecies variations among different species of *Echinacea* collected from nature. As demonstrated in FIG. 5, sequences of different organisms within the same species may also show some sequence variations.

Example 2

Design of PCR Primers for Specific Amplification of Either *Echinacea* or *Parthenieum* Species The sequences of multiple *Echinacea* and *Parthenium* species were aligned (FIG. 6). After multiple alignment of all of the ITS1 and ITS2 sequences of all of the specimens, primers that were specific for either the *Echinacea* or *Parthenium* genus were selected based on inspection of the alignment. The primers were selected such that the primers would amplify most species of either the *Echinacea* or *Parthenium* genus, but not both. To this end, the 3' termini of each primer was located at low information (non-conserved) positions, in which the sequence differences were maximized between the genera. Among the subspecies of *Echinacea* studied here, there were no differences in any of the sequences in the first 50 bp of the amplification product, or positions 100-150 bp. However there was sufficient divergence from the *Parthenium* sequence data to design PCR primers that may be used to distinguish the two genera.

Two sets of primers from each genus were selected based upon the methodology described above. The sequences of the resultant 4 sets of primers are as follows:

```
Primer set 1:
                                          (SEQ ID NO. 84)
Forward: 5'- ACG GGG CGC AAT AGC ACG -3'

(SEQ ID NO. 85)
Reverse: 5'- CGA GGC CTT GTC GAC GTG TG -3'

Primer set 2:
                                          (SEQ ID NO. 86)
Forward: 5'- TGT ATC CAT GAT GCC CCT AT -3'

(SEQ ID NO. 87)
Reverse: 5'- CAA GTA AAA CAC ATG ACC GAG -3'

Primer set 3:
                                          (SEQ ID NO. 88)
Forward: 5'- GAC GGG GCA TAA CAG CAC AA -3'

(SEQ ID NO. 89)
Reverse: 5'- GTG AGG CCT TGT TGA CGA GC -3'

Primer set 4:
                                          (SEQ ID NO. 90)
Forward: 5'- TGT TAG TGT GTC AAC CAG ACA -3'

(SEQ ID NO. 91)
Reverse: 5'- ACA TGT AAA ACT ACT GGC CTT T -3'
```

Example 3

PCR Assay for Identification of *Echinacea* Species

The 4 sets of primers described in Example 2 were tested for amplification at the manufacturer's recommended annealing temperature. Results indicated that the primers recognize their targets. However, under standard reaction conditions, the primers either did not amplify well, or showed a lack of specificity for all tested samples.

To determine the optimal reaction condition, a series of PCR reactions were set up under different annealing temperature and $Mg^{2+}$ concentration. After optimization, the final conditions found to be best suited for amplification with primer sets 1 and set 4 were at 63 degrees for annealing and a master mix concentration of $MgCl_2$ of 2.21 mM for set 4 and 1.91 mM $MgCl_2$ for set 1. Each set of samples was amplified with two series of reactions per primer sets. One was expected to amplify *Parthenium integrefolium* series, the other was expected to amplify only species in the *Echinacea* series. Each series needed a positive control respective of its primers origin. Set 2 & 3 were also tested, and it was found that the highest possible annealing temperature which still routinely gives an appropriately sized product was about 64 degrees.

Tests were carried out on the primers once they had been properly diluted and aliquotted. The ITS1 primers (sets 1 and 4) that were ordered from IDT were for *Echinacea* sp. and *Parthenium integrifolium* sequences. Multiple species of

Figure 7:
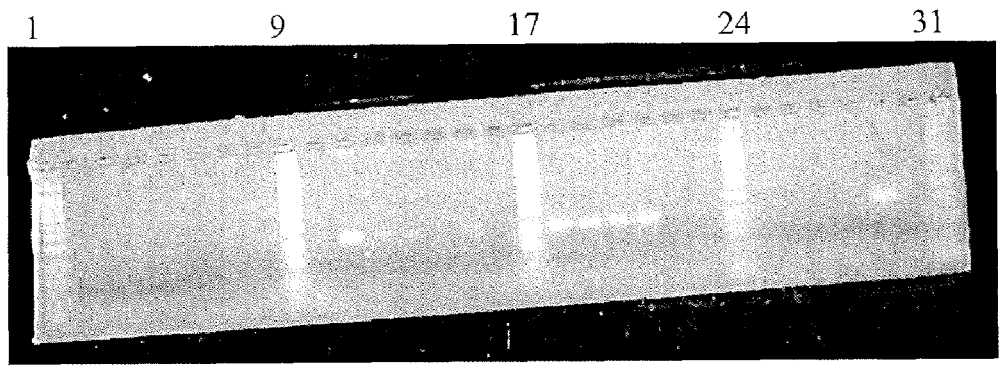
FIG. 7 shows that the *Echinacea* specific primer sets 3 and 4 generate PCR products only when *Echinacea* DNA is present as template, while *Parthenium* specific primers, sets 1 and 2, only amplify *Parthenium* genomic DNA.

*Echinacea* native to continental US were studied, and DNA from multiple exemplars were of each species was isolated. Multiple exemplars of *P. integrifolium* were also collected and DNA isolated. FIG. 7 is the result of such an experiment showing that the *Echinacea* specific primer sets 3 and 4 only generate PCR products when *Echinacea* DNA is present as template, while *Parthenium* specific primers, sets 1 and 2, only amplify *Parthenium* genomic DNA. Primers 3 and 4 may be used for *Echinacea* detection in a background of *Parthenium* or *Rudbeckia* contamination. Primers specific for either *Echinacea* or *Parthineum* may be employed to detect *Echinacea* or *Parthineum* in a mixture that may contain both species. The lane assignments and results shown in FIG. 7 are summarized in Table 2.

TABLE 2

Lane Assignments and PCR Test Results

| Lane assignment: | Result: |
|---|---|
| 1) 100 bp marker | |
| 2) *Parthenium*-specific primers 100-200, sample 3015 | − |
| 3) *Parthenium*-specific primers, sample 4027 | − |
| 4) *Parthenium*-specific primers, sample 2066 | − |
| 5) *Parthenium*-specific primers, sample 5077 | − |
| 6) *Parthenium*-specific primers, sample 1106 | − |
| 7) *Parthenium*-specific primers, sample 4023 (+) | − |
| 8) *Parthenium*-specific primers, sample (−control reaction, no DNA) | − |
| 9) marker | |
| 10) *Echinacea*-specific primers 100-200, sample 3015 | − |
| 11) *Echinacea*-specific primers, sample 4027 | + |
| 12) *Echinacea*-specific primers, sample 2066 | + |
| 13) *Echinacea*-specific primers, sample 5077 | + |
| 14) *Echinacea*-specific primers, sample 1106 | + |
| 15) *Echinacea*-specific primers, sample 4024 | + |
| 16) *Echinacea*-specific primers, sample (−control reaction, no DNA) | − |
| 17) marker | |
| 18) *Parthenium*-specific primers 100-200, sample 6052 | + |
| 19) *Parthenium*-specific primers, sample 6053 | + |
| 20) *Parthenium*-specific primers, sample 6054 | + |
| 21) *Parthenium*-specific primers, sample 6055 | + |
| 22) *Parthenium*-specific primers, sample 4023 | − |
| 23) *Parthenium*-specific primers, sample (−control reaction, no DNA) | − |
| 24) marker | |
| 25) *Echinacea*-specific primers 100-200, sample 6052 | − |
| 26) *Echinacea*-specific primers, sample 6053 | − |
| 27) *Echinacea*-specific primers, sample 6054 | − |
| 28) *Echinacea*-specific primers, sample 6055 | − |
| 29) *Echinacea*-specific primers, sample 4023 | + |
| 30) *Echinacea*-specific primers, sample (−control reaction, no DNA) | − |
| 31) marker | |

Figure 8:
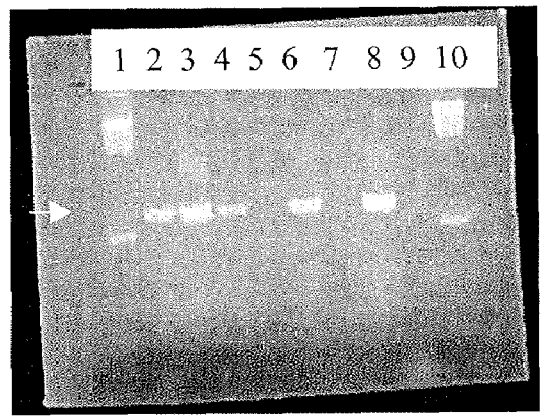
FIG. 8 shows the effects of the source of DNA and the methods of purifying the template DNA on the PCR amplification.

FIG. 8 shows results of an experiment attempted to address the question of whether the source of DNA and the methods used in purifying the template DNA have any effects on the PCR amplification. Lanes 1 and 10 are DNA markers to ensure that the correct size product has been obtained. Lane 9 is a negative control reaction in which no DNA has been added; this ensures that the reagents have not been contaminated with any other DNA source. Lanes 2 (*E. purpurea*) and 3 (*E. pallida*) correspond to amplified DNAs isolated from fresh specimens collected during the year 2000 harvest (arrow). Lane 4 contains amplified DNA from a 5 year old *Echinacea* specimen (1996). Lanes 5 through 8 were amplification reactions of DNA from 2 different *Echinacea* species, each purified by both a commercial procedure (lanes 6 and 8) and another experimental procedure (lanes 5 and 7). No amplification was observed using the experimental DNA purification procedure, however amplification was detected with the commercial kit.

The results in FIG. 8 also show that DNA from powdered *Echinacea purpurea* derived from stored, aged preparations could be amplified with the *Echinacea* specific primer sets. A member of another closely related but distinct genus, *Rudbeckia linti*, was also tested with the *Echinacea* specific primers. No amplification product was produced with *Echinacea* specific primers and *Rudbeckia* DNA template.

Once the parameters for the primer sets had been finalized, the complete library of samples were tested to determine if there were any sub-species that were not compatible with the parameters, or if any artifactual amplification products might be produced. None were detected and all *Echinacea* DNA preparations were amplified. Because of the breadth of the geographic distribution of the samples and the fact that all relevant species were tested, we conclude that a "randomly sampled" plant taken from the field would produce the expected results with this assay primers.

We then carried out Tracer/Driver (T/D) experiments to determine the sensitivity of the assay to detect trace levels of contaminating *Parthenium* or *Rudbeckia* sequences in a presumed homogeneous preparation of *Echinacea* DNA. In these experiments, sample DNA needs to be diluted in known quantities in order to accurately determine the sensitivity of each primer set. The design uses primers to detect various levels of tracer DNA diluted into an excess of driver DNA. The Tracer DNA ranges in concentration from 10,000 to 1 genome equivalents (e.g.), so that each consecutive dilution will have a 10 fold lower concentration. Driver DNA will be added to qsp the weight of total DNA present per dilution to 50 ng for experimental reactions, while no Driver will be added to the Tracer positive dilutions. There will be two sets of T/D experimental dilutions per primer set. One set consists of *Rudbeckia* D DNA, and the other set consists of either *Echinacea* or *Parthenium* D DNA, depending on which primer set is being investigated. Primer Sets 1 & 4 were used. For primer set 4, the sensitivity of detecting *Echinacea* D DNA was 1000 fold lower when compared to the $H_2O$ ge dilutions. The sensitivity of detection with Set 1 was compromised only 10 fold when *Parthenieum* D was present and even less so when *Rudbeckia* D DNA was present. These results show a sensitivity of 16,000 g.e.'s for detection of *Parthenium* and 27,000 g.e.'s for detection of *Echinacea*.

Figure 9:
FIG. 9 shows results of agarose gel electrophoresis of amplified internal transcribed spacer sequences from several *Echinacea* species under different concentrations of $Mg^{2+}$.

FIG. 9 shows results of agarose gel electrophoresis of amplified internal transcribed spacer sequences from several *Echinacea* species under different concentrations of $Mg^{2+}$. DNA was extracted from washed, pulverized root material of *Echinacea angustifolia* (2 samples), *E. atrorubens* (2 samples), *E. pallida* (1 sample) and *E. purpurea* (3 samples). PCR amplification of the internal transcribed spacer ITS1 sequences of 23S rDNA using Primer Set 3 generated DNA products of appropriate size for all species except *Echinacea pallida*. The concentration of $Mg^{2+}$ appears to have a drastic effect on the PCR results.

REFERENCES CITED

Aceto et al. Phylogeny and evolution of Orchis and allied genera based on ITS DNA variation: morphological gaps and molecular continuity. Mol Phylogenet Evol. 1999 October; 13(1):67-76

Mullis K B, Faloona F A, "Specific synthesis of DNA in vitro via a polymerase-catalyzed chain reaction," Methods Enzymol. 1987; 155:335-50.

Stimpel et al Infection and Immunity, 46(3), 845-849, 1984

Roesler, et al. J. Immunopharmac., 13(1), 27-37, 1991a

Roesler, et al, J. Immunopharmac., 13 (7), 931-941, 1991b

Braunig, B., M. Dorn, E. Limburg, and E. Knick. 1992. *Echinacea purpurea* Radix For Strengthening the Immune Response in Flu-like Infections. Zeitschrift fur Phytotherapie 13:7-13 (In German; translated by Shanti Coble and Christopher Hobbs).

Schoneberger, D. 1992. The Influence of Immune-Stimulating Effects of Pressed Juice from *Echinacea purpurea* on the Course and Severity of Colds. Forum Immunologie 8:2-12. (In German, translated by Sigrid M. Klein).

Mengs et al. Toxicity of *Echinacea purpurea*. Acute, subacute and genotoxicity studies. Arzneimittelforschung. 1991 October; 41(10): 1076-81.

McGregor, Univ. Kansas Sci Bull. 98: 113-42, 1968

Jupe E R & Zimmer E A. *Plant Mol Biol* 1990 March; 14(3): 333-47

Reamon-Buttner S M, Schmidt T, Jung C. *Chromosome Res* 1999; 7(4):297-304

Woese, C. Bacterial evolution. Microbiol Rev. 1987 June; 51(2):221-71

Binns, S. E., Baum, B. R., and Arnason, J. T. 2002. A taxonomic revision of *Echinacea* (Asteraceae: Heliantheae). Syst. Bot. 27: 610-632.

Kim et al. Kim D H, Heber D, Still D W. Genetic diversity of *Echinacea* species based upon amplified fragment length polymorphism markers. Genome. 2004 February; 47(1): 102-11.

Bobowski et al. Identification of roots of woody species using polymerase chain reaction (PCR) and restriction fragment length polymorphism (RFLP) analysis. Mol Ecol. 1999 March; 8(3):485-91.

Bauer R. et al., H. Deutsche Apothekaer Zeitung, 127 Jahrg., Nr. 25, 18, 6 (1987), 1325-1330;

Bauer, R. in Phytomedicines of Europe: Chemistry and Biological Activity; ACS Symosium Series 691, ed. Lawson, L. and Bauer, R. (1998), 140-157.

Rogan P K, Salvo J J, Stephens R M, Schneider T D. In: *Visualizing Biological Information*, C A Pickover (ed). World Scientific, River Edge N.J., 1995

Tooley P W, Salvo J J, Schneider T D, Rogan P K. J Phytopathology, 146(8-9): 427-430, 1998

Soltis P and Soltis D. The role of genetic and genomic attributes in the success of polyploids Proc Natl Acad Sci USA. 2000 Jun. 20; 97(13):7051-7.

Francisco-Ortega J, Fuertes-Aguilar J, Gomez-Campo C, Santos-Guerra A, Jansen R K Internal transcribed spacer sequence phylogeny of Crambe L. (Brassicaceae): molecular data reveal two Old World disjunctions. Mol Phylogenet Evol. 1999 April; 11(3):361-80.

E Emshwiller, J J Doyle. Origins of domestication and polyploidy in oca (*Oxalis tuberosa*: Oxalidaceae): nrDNA ITS data. American Journal of Botany 85(7): 975-985. 1998

Gielly et al. Phylogenetic use of noncoding regions in the genus *Gentiana* L.: chloroplast trnL (UAA) intron versus nuclear ribosomal internal transcribed spacer sequences. Mol Phylogenet Evol. 1996 June; 5(3):460-6.

Jobst et al. Molecular evolution of the internal transcribed spacers (ITS1 and ITS2) and phylogenetic relationships among species of the family Cucurbitaceae. Mol Phylogenet Evol. 1998 April; 9(2):204-19.

Ainouche M and Bayer R. On the origins of the tetraploid *Bromus* species (section *Bromus*, Poaceae): insights from internal transcribed spacer sequences of nuclear ribosomal DNA. Genome. 1997 October; 40(5):730-43.

Liu J and Schardl C. A conserved sequence in internal transcribed spacer 1 of plant nuclear rRNA genes. Plant Mol Biol. 1994 October; 26(2):775-8.

Koopman, W. J. M., Guetta, E., van de Wiel, C. C. M., Vosman, B. and van den Berg, R. G., Am. J. Bot. 85, 1517-1530, 1998

Van der Stappen, J., van Campenhout, S. and Volckaert, G, Theor. Appl. Genet. 96, 869-877, 1998.

---

What is claimed is:

1. A pair of oligonucleotide molecules for amplification of ribosomal DNA from a plant material, said oligonucleotide molecules being selected from the group consisting of primer set 1 and primer set 2, wherein primer set 1 comprises the oligonucleotides of SEQ ID Nos. 84 and 85, primer set 2 comprises the oligonucleotides of SEQ ID Nos. 86 and 87.

2. A pair of oligonucleotide molecules for amplification of ribosomal DNA from a plant material, said oligonucleotide molecules being selected from the group consisting of primer set 3 and primer set 4, wherein primer set 3 comprises the oligonucleotides of SEQ ID Nos. 88 and 89, primer set 4 comprises the oligonucleotides of SEQ ID Nos. 90 and 91.

3. A method for determining the existence of an organism or its derivatives in a material, said method comprising:
   (1) a first DNA amplification of a segment on a ribosomal DNA, wherein a first primers pair is used as PCR primer and DNA from at least one species belonging to the same genus as said organism is used as template;
   (2) sequencing the PCR product resulting from the first amplification;
   (3) a second DNA amplification using as PCR primers a second primer pair and using as template DNA prepared from said material;
wherein the selection of the first primer pair comprises the steps of:
   (a) searching for a divergent segment of the DNA from said at least one species with low average information content determined quantitatively surrounded by two conserved segments of said DNA with high average information content determined quantitatively; and
   (b) designing the first primer pair for PCR amplification of said divergent segment by constructing a sequence logo for said DNA such that said primers contain a set of sequences present in said sequence logo that encompass the nucleotide variability of said conserved segments, said primer pair being able to anneal to said conserved segments for amplification of said divergent segment;
and the selection of the second primer pair comprises the steps of:
   (a) searching the sequences obtained from step (2) for at least one segment of DNA with interspecies variations; and
   (b) designing the second primer pair for DNA amplification, wherein said second primer pair comprises at least one interspecies variation;
   and
   (4) determining the existence of said organism or its derivatives in said material.

4. The method of claim 3, wherein the PCR product resulting from the first amplification comprises an internal transcribed spacer (ITS) region.

5. The method of claim 3, wherein the second primer pair is selected from the group consisting of primer set 1, primer set 2, primer set 3, and primer set 4; and primer set 1 comprises the oligonucleotides of SEQ ID Nos. 84 and 85, primer set 2 comprises the oligonucleotides of SEQ ID Nos. 86 and 87, primer set 3 comprises the oligonucleotides of SEQ ID Nos. 88 and 89, and primer set 4 comprises the oligonucleotides of SEQ ID Nos. 90 and 91.

6. A method for determining the existence of an *Echinacea* species or its derivatives in a sample based on primary structure of DNA from said *Echinacea*, said method comprising:
   (1) amplification of a segment of the internal transcribed spacer region of the ribosomal DNA of said plant material, and
   (2) determining the existence of said *Echinacea* species or its derivatives in said sample,
      said amplification being performed using a pair of oligonucleotides selected from the group consisting of primer set 1, primer set 2, primer set 3, and primer set 4, wherein primer set 1 comprises the oligonucleotides of SEQ ID Nos. 84 and 85, primer set 2 comprises the oligonucleotides of SEQ ID Nos. 86 and 87, primer set 3 comprises the oligonucleotides of SEQ ID Nos. 88 and 89, and primer set 4 comprises the oligonucleotides of SEQ ID Nos. 90 and 91.

7. The method of claim 6 wherein the amplified segment comprises at least one DNA fragment from an internal transcribed spacer region selected from the group consisting of ITS1 and ITS2.

8. The method of claim 6 wherein the segment is amplified using primers that specifically amplify DNA from *Echinacea* species but do not amplify DNA from *Parthenium* species.

9. The method of claim 6 wherein the segment is amplified using primers that specifically amplify DNA from Parthenium species but do not amplify DNA from *Echinacea* species.

10. The method of claim 6 further comprising a step of sequencing said amplified segment.

11. The method of claim 6 wherein DNA prepared from the sample is used as a template for said amplification.

12. The method of claim 11 wherein said sample has been stored for at least 6 months.

13. The method of claim 11 wherein the sample contains specimen from at least two species selected from the group consisting of *Echinacea, Parthineum* and *Rudbeckia.*

14. The method of claim 11 wherein the sample contains specimen from *Echinacea* and *Parthineum.*

* * * * *

SEQUENCE LISTING

```
<160> NUMBER OF SEQ ID NOS: 91

<210> SEQ ID NO 1
<211> LENGTH: 257
<212> TYPE: DNA
<213> ORGANISM: Echinacea paradoxa

<400> SEQUENCE: 1
tcgaatcctg catagcagaa cgacccgtga acatgtaaaa actactggcc tttcggggac      60
cgaagcattt gtttcgagcc ttgtgaggcc ttgttgacga gcattcatgc ttgcctctac     120
ggggcatcat ggttgtctgg ttgacacact aacaaccccc gcacaacatg tgccaaggaa     180
aacaaaactt aaagggcttg tgctgttatg ccccgtcatt ggtgtgcata ctgtgcgttg     240
cttcttttgt aaacttt                                                    257

<210> SEQ ID NO 2
<211> LENGTH: 256
<212> TYPE: DNA
<213> ORGANISM: Echinacea simulata

<400> SEQUENCE: 2
```

```
tcgaatcctg catagcagaa cgacccgtga acatgtataa actactggcc tttcggggac    60
cgaagcattt gtttcgagcc ttgtgaggcc ttgttgacga gcattcatgc ttgcctctac   120
ggggcatcat ggttgtctgg ttgacacact aacaaccccc gcacaacatg tgccaaggaa   180
aacaaaactt aaagggcttg tgctgttatg ccccgtcaat tggtgtgcat actgtgcgtt   240
gcttcttttg taaact                                                   256
```

```
<210> SEQ ID NO 3
<211> LENGTH: 257
<212> TYPE: DNA
<213> ORGANISM: Echinacea pallida

<400> SEQUENCE: 3
tcgaatcctg catagcagaa cgacccgtga acatgtaaaa actactggcc tttcggggac    60
cgaagcattt gtttcgagcc ttgtgaggcc ttgttgacga gcattcatgc ttgcctctac   120
ggggcatcat ggttgtctgg ttgacacact aacaaccccc ggcacaacat gtgccaagga   180
aaacaaaact taagggcttg tgctgttat gccccgtcat tggtgtgcat actgtcgttg    240
cttcttttgt aaacttt                                                  257
```

```
<210> SEQ ID NO 4
<211> LENGTH: 259
<212> TYPE: DNA
<213> ORGANISM: Echinacea purpurea

<400> SEQUENCE: 4
tcgaatcctg catagcataa cgacccgtga acatgtaaaa actactggcc tttcagggga    60
ccgaaagcat ttgtttcggc cttgtgaggc cttgttgacg agcattcatg cttgcctcta   120
cggggcatca tggttgtctg gttgacacac taacaacccc cggcacaaca tgtgccaagg   180
aaaacaaaac ttaagggct tgtgctgtta tgccccgtca ttggtgtgca tagtgtgcgt    240
tgcttctttt gtaaacttt                                                259
```

```
<210> SEQ ID NO 5
<211> LENGTH: 258
<212> TYPE: DNA
<213> ORGANISM: Echinacea tennesseensis

<400> SEQUENCE: 5
tcgaatcctg atagcagaac gacccgtgaa catgtaaaaa ctacttggtc tttcggggga    60
ccgaagcatt tgtttgagcc ttgtgaggcc ttgttgacga gcattcatgc ttgcctctac   120
ggggcatcat ggttgtctgg ttgacacact aacaaccccc ggcacaacat gtgccaagga   180
aaacaaaact taagggcttg tgctgttat gccccgtcat tggtgtgcat actgtgcgtt    240
gcttcttttg taaacttt                                                 258
```

```
<210> SEQ ID NO 6
<211> LENGTH: 256
<212> TYPE: DNA
<213> ORGANISM: Echinacea atrorubens

<400> SEQUENCE: 6
tcgaaccctg catagcagaa cgacccgtga acatgtaaaa atactggcct ttcggggacc    60
gaaggcattt gtttcgagcc ttgtgaggcc ttgttgacga gcattcatgc ttgcctctac   120
ggggcatcat ggttgtctgg ttgacacact aacaaccccc ggcacaacat gtgccaagga   180
aaacaaaact taagggcttg tgctgttat gccccgtcaa ttggtgtgca tactgtgcgt    240
```
tgcttctttg taaact                                                      256

<210> SEQ ID NO 7
<211> LENGTH: 292
<212> TYPE: DNA
<213> ORGANISM: Echinacea

<400> SEQUENCE: 7
ramracgacc gacagtatgc acaccaatga cggggcataa cagcacaagc ctttaagttt     60
tgttttcctt ggcacatktt gtgccggggg ttgttagtgt gtcaaccaga caaccawgrt    120
gccccgkaga ggcarcmtgr atkctcstca acaargcctc acaaggstcs aaacaaatgc    180
ttcggkcccc saaaaggcca rtagttttta catgttcacg ggkcgttctg ctatgcagrt    240
tygacaatga tckmdccgcm ggrtcacyac gggaamcttt gtacgctttt wc            292

<210> SEQ ID NO 8
<211> LENGTH: 294
<212> TYPE: DNA
<213> ORGANISM: Echinacea

<400> SEQUENCE: 8
acaagagcam gcacagtatg srcascmaat dacggggcak aacavcacaa gcctttaagy     60
tttgttttcc ttggcacatk ttgtgccggg ggttgttagt gtgtcaacca dacaaccatg    120
atgcccgtag aggcaagcat gaatgctcgt caacaaggcc tcacaaggct cgaaacaaat    180
gcttcggtcc cygaaaggsc agtagttttwt acatgttcac gggtsgttct gctatgcagg    240
rttcgacawg atshgkcaac scaggttcmc yacrgraaam yttgtacrca ttta          294

<210> SEQ ID NO 9
<211> LENGTH: 296
<212> TYPE: DNA
<213> ORGANISM: Echinacea

<400> SEQUENCE: 9
wcaaaaragc acgcacagta tgcmcacaat dacggggcmt aacagcacaa gcctttaagt     60
tttgttttcc ttggcacatk ttgtgccggg ggttgttagt gtgtcaacca dacaaccawk    120
rwgccccska gaggcaagcm tkaatgctcg tcaacaargc ctcacaaggs tcsaaacaaa    180
tgcttcggtc ccgaaaargsc agtwgttttwt acatgttcac ggkcgttctg ctatgcaggr    240
ttcgacaatg atccttccgc aggktcacct acggraacct tgttacgact tttwmt         296

<210> SEQ ID NO 10
<211> LENGTH: 236
<212> TYPE: DNA
<213> ORGANISM: Echinacea

<400> SEQUENCE: 10
maargcacgc acagtatgca cacatrcggg gcatamgmmr cctttagttt gttcttggmc     60
atkttgtgcg ggggttgtag tgtgtcacya gacacatgat gccgtagagc agcatgatgc    120
tcgtcacarg ctcacagstc gaacaatgct tcgtcyragg cagtagttwt acatgtcacg    180
ggygtctgct akcagrtcga cawgawctcg crgtcacyac gractgtacg mttwct        236

<210> SEQ ID NO 11
<211> LENGTH: 234
<212> TYPE: DNA
<213> ORGANISM: Echinacea

<400> SEQUENCE: 11

```
tmaagasmgc magtatgcma catgacgggc atacagcaca gctttagttg ttcttggcac    60
atktgtgcgg gggtgtagtg tgtcacagac aacatgatgc ckagagcagc atgatgctcg   120
tcacaggctc acagctcgaa caatgctcgg tccsaaggca gtagttatac atgtcacggt   180
cgtctgctat sagatcgaca tgatctcgcr gtcactacga actgtacrct tact          234
```

<210> SEQ ID NO 12
<211> LENGTH: 236
<212> TYPE: DNA
<213> ORGANISM: Echinacea

<400> SEQUENCE: 12

```
yaaragcacg mcagwtgcac acatgacggg gcatacagca cagctttagt ttgtttcttg    60
gmcatkttgt rcgggggttg tagtgtgtca cagacaacat gwgccgtaga gcagcatgat   120
gctcgyacag gctcmagctc gaacaatgct cggtcccgaa gcagtagttw tacatgtcac   180
ggkcgtctgy atsagrtcga cawgatctcg crgtcactac gaactgtacg acttac       236
```

<210> SEQ ID NO 13
<211> LENGTH: 240
<212> TYPE: DNA
<213> ORGANISM: Echinacea

<400> SEQUENCE: 13

```
argcacgcac agwtgcacac atgacggggm tacagcacaa gctttaagtt ttgttttcyt    60
ggmcatkttg trcggggtg tagtgtgyac agacacatgw gcccgtagag cagcatgatg   120
ctcgyacagg ctcacagstc gaacatgctc rgtccgaagg cagtagttwt acatgtcacg   180
gkcgtctgct atsagrtcga catgatcttc gcagtcacta cgractgtac agmttacgtc   240
```

<210> SEQ ID NO 14
<211> LENGTH: 239
<212> TYPE: DNA
<213> ORGANISM: Echinacea

<400> SEQUENCE: 14

```
ymaasagcac gcacagtatg cacacatgac ggggcatamg mcagccttta agtttgttct    60
tggmcatktt gtgcgggggt tgtakgtgtc acarcacayg wgcccgyrag carcmtgatg   120
cycgtcacar gctcmcagst cgmacaatgc tcgtcysmag castagttwt acatgtcacg   180
gkcgtctgct mtgcmggatc gmcamtgayc ycgcmgtcmc tacggaacmy gtasactta    239
```

<210> SEQ ID NO 15
<211> LENGTH: 218
<212> TYPE: DNA
<213> ORGANISM: Echinacea

<400> SEQUENCE: 15

```
kwmarmgmcg mmgwkmmcaa trcgmagcct twagtttgtt ttcttggmmk tttgwgcggg    60
ggttgtagtg tgyaacagac acatgatgcc cgwgagcagm tgatgctcgt cacargctca   120
cargstcgaa caatgctcgt ckaagcagwg twwcatgtca cggkcgtctg ctakcagrtc   180
rcatgatctt cgcagtcact acgractgta sacttact                            218
```

<210> SEQ ID NO 16
<211> LENGTH: 254
<212> TYPE: DNA
<213> ORGANISM: Echinacea

<400> SEQUENCE: 16

```
tmaaragcac gcacrtwgcm acaatgacgg ggcatacagm caagccttta agtttgtttt      60
cttggcacat kttgtgcggg ggttgtagtg tgyaaccaga caacatgatg cccgtagagg     120
caagcatgaa tgctcgtcaa caggctcaca gctcgaacaa atgctcgtcc yraggcagta    180
gttwtacatg tcacggkcgt ctgctakcrg rtcgacatga tcttcgcagt cactacgraa    240
cwtgtacgac ttac                                                        254
```

<210> SEQ ID NO 17
<211> LENGTH: 249
<212> TYPE: DNA
<213> ORGANISM: Echinacea

<400> SEQUENCE: 17

```
magagsacgc acagtatgca cacatgacgg gcatacagca cagcctttaa gtttgttctt      60
ggcacatktt gtrcggggt tgtakgtgya ccagacaaca tgatgccgta gaggcaagca    120
tgaatgctcg tcacaggctc acaaggctcg aacaatgctc ggtccragca gtagttwtac   180
atgtcacggg tcgtctgcta kcagatcgma tgatcttcgc agttcactac ggaactgtac   240
gamttttay                                                              249
```

<210> SEQ ID NO 18
<211> LENGTH: 295
<212> TYPE: DNA
<213> ORGANISM: Parthenium

<400> SEQUENCE: 18

```
rwagtgcacg tacatgcgca cacgcgaacg gggcgcaata gcacgggccc tttaartttta     60
rttttccttg gcacgtacgg tgccggggggt ttgttattgt gtcaacatgt atccatgatg   120
ccccatatgt atggtgcagc cataaacaca cgtcgacaag gcctcrcgag gctcgaaaca   180
taagctccgg tcctcgctcg gtcatgtgtt tttacttgtt cacgggtcgt tctgctatgc   240
agggttcgac aatgatcyah cgcaggttca ctacggaaac ttgtacgact wtaac          295
```

<210> SEQ ID NO 19
<211> LENGTH: 289
<212> TYPE: DNA
<213> ORGANISM: Parthenium

<400> SEQUENCE: 19

```
gtgcacgtac atgcgcrcrc gcgaacgggg cgcaatagca cgggccttta agtttagttt     60
tccttggcac gtacggtgcc gggggtttgt tattgtgtca acatgtatcc atgatgcccc   120
rtatgtatgg tgcagccata aacacacgtc gacaaggcct cacgaggctc gaaacataar   180
ctccggtcct cgctcggtca tgtgttttta cttkttcacg ggtcgttctg ctatgmgggt   240
tcgamaatga tcctdccgca gtttmctacg aaaacttgtw acaatttwa                  289
```

<210> SEQ ID NO 20
<211> LENGTH: 299
<212> TYPE: DNA
<213> ORGANISM: Parthenium
<220> FEATURE:
<221> NAME/KEY: misc_feature
<222> LOCATION: (262)..(262)
<223> OTHER INFORMATION: n is a, c, g, or t

<400> SEQUENCE: 20

```
wagtgcacgt acatgcgcac mccgcgaacg gggcgcaata gcacgggcct ttaagtttag      60
ttttccttgg cacgtacggt gccgggggtt tgttattgtg tcaacatgta tccatgatgc     120
cccatatgta tggtgcagcc ataaacacac gtcgacaagg cctcacgagg ctcgaaacat     180
aagctccggt cctcgctcgg tcatgtgttt ttacttgttc acgggtcgtt ctgctatgca     240
gggkttcgam aatgatccst vnsgcaggtt cmccyacgga aacctkgtam gacttttac     299
```

<210> SEQ ID NO 21
<211> LENGTH: 294
<212> TYPE: DNA
<213> ORGANISM: Parthenium

<400> SEQUENCE: 21

```
wgtgcacgwc aatgcgcaca cgcgaacggg gcgcaatagc acgggccttt aagtttagtt      60
ttccttggca cgtacggtgc cgggggttts ttattgtgtc aacatstatc catgatgccc     120
rtcatgtatg gtgcagccat aaamacacgt cgacaaggct cscgmggstc gmaacataar     180
syccsgtcct cvtcggtcat gtgttttacy tgttccccgs gkcgsttctg cyatgmgggg     240
tcgmccmtga yccywcccgc mggkcmccym ccggsgaccc tstwccgmcy ttta           294
```

<210> SEQ ID NO 22
<211> LENGTH: 247
<212> TYPE: DNA
<213> ORGANISM: Echinacea angustifolia

<400> SEQUENCE: 22

```
vcwtctwrtg tctggttggg gsggagattg gtctccgtgc acttgcatgg ttgacctaaa      60
tatgagtctc ctcacgagag acgcacggct agtggtggtt gataacacag tcgtctcgtg     120
ccgtacgttt atgtttgtga gtgtctagac ttgtgaaaaa mctgacgcgt cgtcttcaga     180
tgatgcttcg atcgcgaccc caggtcaggs gggactaccs cygagtttaa rcatatcaat     240 aarcgga                                                                247
```

<210> SEQ ID NO 23
<211> LENGTH: 248
<212> TYPE: DNA
<213> ORGANISM: Echinacea angustifolia

<400> SEQUENCE: 23

```
yatttagatg tctggttggg gcggagattg gtctcccgtg ccacttgcat ggttgaccta      60
aatatgagtc tctcacgaga gacgcacggc tagtggtggt tgataacaca gtcgtctcgt     120
gccgtacgtt tatgtttgtg agtgtctaga cttgtgaaaa cctgacgcgt cgtcttcaga     180
tgatgcttcg atcgcgaccc cagggtcagg sgggactacc cgctgagtta agcatatcaa     240 taagsgga                                                               248
```

<210> SEQ ID NO 24
<211> LENGTH: 214
<212> TYPE: DNA
<213> ORGANISM: Echinacea angustifolia

<400> SEQUENCE: 24

```
tgytggtggg gcggagattg gtctccgtgc acttgcatgg ttgactaata tgrtctctca      60
cgrrmgcacg gctagtggtg gttgatacac agtcgtctcg tgcgtacgtt tatgtttgtg     120
agtgtctaga cttgtgaaac tgacgcgtcg tcttcagatk atgcttcgwc gcgacccagt     180
cagsgggmta ccsctgrttw asatatmawa sgga                                 214
```

<210> SEQ ID NO 25
<211> LENGTH: 297
<212> TYPE: DNA
<213> ORGANISM: Parthenium integrifolium

<400> SEQUENCE: 25
aagtgcacgt acatgcgcac accgcgaacg gggcgcaata gcacgggcct ttaagtttag    60
ttttccttgg cacgtacggt gccggggtt tgttattgtg tcaacatgta tccatgatgc    120
cccrtatgta tggtgcagcc ataaacacac gtcgacaagg cctcacgagg ctcgaaacat    180
aagctccggt cctcgctcgg tcatgtgttt ttacttgttc acgggtcgtt ctgctatgca    240
gggttcgaca atgatcchc gcaggttcac cctacggaaa ccttgtacga ctttact       297

<210> SEQ ID NO 26
<211> LENGTH: 295
<212> TYPE: DNA
<213> ORGANISM: Parthenium integrifolium
<220> FEATURE:
<221> NAME/KEY: misc_feature
<222> LOCATION: (258)..(259)
<223> OTHER INFORMATION: n is a, c, g, or t

<400> SEQUENCE: 26
aagtgcacgt acatgcgcac accgcgaacg gggcgcaata gcacgggcct ttaagtttag    60
ttttccttgg cacgtacggt gccggggtt tgttattgtg tcaacatgta tccatgatgc    120
cccrtatgta tggtgcagcc ataaacacac gtcgacaagg cctcacgagg ctcgaaacat    180
aagctccggt cctcgctcgg tcatgtgttt ttacttgttc acgggtcgtt ctgctatgca    240
gggttcgaca atgatccnnc gcaggttcac ctacggaacc tgtacgact ttact         295

<210> SEQ ID NO 27
<211> LENGTH: 297
<212> TYPE: DNA
<213> ORGANISM: Parthenium integrifolium
<220> FEATURE:
<221> NAME/KEY: misc_feature
<222> LOCATION: (260)..(260)
<223> OTHER INFORMATION: n is a, c, g, or t

<400> SEQUENCE: 27
aagtgcacgt acaatgcgca caccgcgaac ggggcgcaat agcacgggcc tttaagttta    60
gttttccttg gcacgtacgg tgccgggggt ttgttattgt gtcaacatgt atccatgatg    120
ccccrtatgt atggtgcagc cataaacaca cgtcgacaag gcctcacgag gctcgaaaca    180
taagctccgg tcctcgctcg gtcatgtgtt tttacttgtt cacgggtcgt tctgctatgc    240
agggttcgac aatgatccvn cgcaggttca cctacggaaa ccttgtacga ctttact      297

<210> SEQ ID NO 28
<211> LENGTH: 296
<212> TYPE: DNA
<213> ORGANISM: Parthenium integrifolium

<400> SEQUENCE: 28
aagttgcacg tacaatgcgc acaccgcgaa cggggcgcaa tagcacgggc cctttaagtt    60
tagttttcct tggcacgtac ggtgccgggg gtttgttatt gtgtcaacat gtatccatga    120
tgccccrtat gtatggtgca gccataaaca cacgtcgaca aggcctcgcg aggctcgaaa    180
cataagctcc ggtcctcgct cggtcatgtg ttttacttgt tcacgggtcg ttctgctatg    240

```
cagggttcga caatgatcct wcgcaggttc acctacggaa cttgtacgac tttact        296
```

```
<210> SEQ ID NO 29
<211> LENGTH: 300
<212> TYPE: DNA
<213> ORGANISM: Echinacea purpurea

<400> SEQUENCE: 29
ttacaaaaga agcaacgcac agtatgcaca ccaatgacgg ggcataacag cacaagccct     60
ttaagttttg ttttccttgg cacatkttgt gccgggggtt gttagtgtgt caaccagaca   120
accatgatgc cccgtagagg caagcatgaa tgctcgtcaa caaggcctca caaggctcga   180
aacaaatgct tcggtccccg aaaggccagt agttttttaca tgttcacggg tcgttctgct   240
atgcaggatt cgacaatgat ccgcaggttc acctacggaa accttgttac gacttttact    300
```

```
<210> SEQ ID NO 30
<211> LENGTH: 304
<212> TYPE: DNA
<213> ORGANISM: Echinacea paradoxa
<220> FEATURE:
<221> NAME/KEY: misc_feature
<222> LOCATION: (263)..(264)
<223> OTHER INFORMATION: n is a, c, g, or t

<400> SEQUENCE: 30
tacaaaagaa gcaacgcaca gtatgcacac caatgacggg gcataacagc acaagccctt     60
taagttttgt tttccttggc acatkttgtr ccggggttg ttagtgtgtc aaccagacaa    120
ccatgatgcc ccgtagaggc aagcatgaat agctcgtcaa caaggcctca caaggctcga   180
aacaaaatgc ttcggtcccc gaaaggccag tagtttwtac atgttcacgg gtcgttctgc    240
tatgcaggat tcgacaatga tcnnccgcag gttcacctac ggaaaccttg ttacgacttt    300
tact                                                                304
```

```
<210> SEQ ID NO 31
<211> LENGTH: 297
<212> TYPE: DNA
<213> ORGANISM: Echinacea pallida

<400> SEQUENCE: 31
caaaagaagc aacgcacagt atgcacacca atracggggc ataacagcac aagcccttta     60
agttttgttt tccttggcac atkttgtgcc ggggttgtt agtgtgtcaa ccagacaacc   120
atgatgcccc gtagaggcaa gcatgaatgc tcgtcaaca ggcctcacaa ggctcgaaac   180
aaatgcttcg gtccccgaaa ggccagtagt ttwtacatgt cacgggtcgt tctgctatgc    240
aggattcgac atgatccwwc cgcaggttca cctacggaaa ccttgtacga ctttact      297
```

```
<210> SEQ ID NO 32
<211> LENGTH: 300
<212> TYPE: DNA
<213> ORGANISM: Echinacea atrorubens

<400> SEQUENCE: 32
acaaaagaag caacgcacag tatgcacacc aatgacgggg cataacagca caagcccttt     60
aagttttgtt ttccttggca catkttgtgc cggggttgt tagtgtgtca accagacaac   120
catgatgccc cgtagaggca agcatgaatg ctcgtcaaca aggcctcaca aggctcgaaa   180
caaaatgctt cggtcccccga aasgccagta gtttwtacat gtcacgggtc gttctgctat    240
gcaggattcg acaatgatcc ttccgcaggt tcacctacgg aaaccttgta cgactttact    300
```

<210> SEQ ID NO 33
<211> LENGTH: 297
<212> TYPE: DNA
<213> ORGANISM: Echinacea pallida
<220> FEATURE:
<221> NAME/KEY: misc_feature
<222> LOCATION: (258)..(259)
<223> OTHER INFORMATION: n is a, c, g, or t

<400> SEQUENCE: 33
caaaagaagc aacgcacagt atgcacacca atracggggc ataacagcac aagcccttta      60
agttttgttt tccttggcac atkttgtgcc ggggggttgtt agtgtgtcaa ccagacaacc    120
atgatgcccc gtagaggcaa gcatgaatgc tcgtcaacaa ggcctcacaa ggctcgaaac    180
aaatgcttcg gtccccgaaa ggccagtagt twtacatgtt cacgggtcgt ctgctatgca    240
ggattcgaca atgatccnnc cgcaggttca cctacggaaa ccttgtacga ctttact       297

<210> SEQ ID NO 34
<211> LENGTH: 301
<212> TYPE: DNA
<213> ORGANISM: Echinacea angustifolia

<400> SEQUENCE: 34
ttacaaaaga agcaacgcac agtatgcaca ccaatgacgg ggcataacag cacaagccct     60
taagttttg ttttccttgg cacatkttgt gccgggggtt gttagtgtgt caaccagaca    120
accatgatgc cccgtagagg caagcatgaa tgctcgtcaa caaggctcac aaggctcgaa    180
acaaatgctt cggtccccga aaggccagta gtttatacat gttcacgggt cgttctgcta    240
tgcaggattc gacaatgatc ttccgcaggt tcacctacgg aaaccttgta cgacttttac    300
t                                                                   301

<210> SEQ ID NO 35
<211> LENGTH: 294
<212> TYPE: DNA
<213> ORGANISM: Echinacea pallida
<220> FEATURE:
<221> NAME/KEY: misc_feature
<222> LOCATION: (259)..(262)
<223> OTHER INFORMATION: n is a, c, g, or t

<400> SEQUENCE: 35
tacaaaagaa gcaacgcaca gtatgcacac caatgacggg gcataacagc acaagccctt     60
taagttttgt tttccttggc acatgttgtg ccggggggttg ttagtgtgtc aaccagacaa   120
ccatgatgcc ccgtagaggc aagcatgaat gctcgtcaac aaggctcaca aggctcraaa    180
caaatgcttc ggtccccgaa aggccagtag tttwtacatg tcacgggtcg ttctgctatg    240
caggattcga caatgatcnn nncgcaggtt cacctacgga aaccttgtac gact          294

<210> SEQ ID NO 36
<211> LENGTH: 301
<212> TYPE: DNA
<213> ORGANISM: Echinacea purpurea
<220> FEATURE:
<221> NAME/KEY: misc_feature
<222> LOCATION: (262)..(265)
<223> OTHER INFORMATION: n is a, c, g, or t

<400> SEQUENCE: 36
ttacaaaaga agcaacgcac agtatgcaca ccaatgacgg ggcataacag cacaagccct     60

```
ttaagttttg ttttccttgg cacatkttgt gccgggggtt gttagtgtgt caaccagaca    120
accatgatgc cccgtagagg caagcatgaa tgctcgtcaa caaggcctca caaggctcga    180
aacaaatgct tcggtccccg aaaggccagt agttttttaca tgttcacggg tcgttctgct   240
atgcaggatt cgacaatgat cnnnncgcag gttcaccwkg gaaaccttgt acgactttta   300
c                                                                   301
```

<210> SEQ ID NO 37
<211> LENGTH: 294
<212> TYPE: DNA
<213> ORGANISM: Echinacea atrorubens
<220> FEATURE:
<221> NAME/KEY: misc_feature
<222> LOCATION: (255)..(257)
<223> OTHER INFORMATION: n is a, c, g, or t

<400> SEQUENCE: 37

```
agaagcaacg cacagtatgc acaccaatga cggggcataa cagcacaagc cctttaagtt    60
ttgttttcct tggcacatgt tgtgccgggg gttgttagtg tgtcaaccag acaaccatga   120
tgccccgtag aggcaagcat gaatgctcgt caacaaggcc tcacaaggct cgaaacaaat   180
gcttcggtcc cygaaabgcc agtagttttwt acatgttcac gggtcgttct gctatgcagg   240
attcgacaat gatcnnnccg caggttcacc tacgaaacct tgtacgactt tact          294
```

<210> SEQ ID NO 38
<211> LENGTH: 296
<212> TYPE: DNA
<213> ORGANISM: Echinacea atrorubens

<400> SEQUENCE: 38

```
agaagcaacg cacagtatgc acaccaatga cggggcataa cagcacaagc cctttaagtt    60
ttgttttcct tggcacatkt tgtgccgggg gttgttagtg tgtcaaccag acaaccatga   120
tgccccgtag aggcaagcat gaatgctcgt caacaaggcc tcacaaggct cgaaacaaat   180
gcttcggtcc cyraaabgcc agtagttttwt acatgttcac gggtcgttct gctatgcagg   240
attcgacaat gatccttccg caggttcacc tacggaaacc ttgtacgact tttact        296
```

<210> SEQ ID NO 39
<211> LENGTH: 303
<212> TYPE: DNA
<213> ORGANISM: Echinacea atrorubens

<400> SEQUENCE: 39

```
ttacaaaaga agcaacgcac agtatgcaca ccaatgacgg ggcataacag cacaagccct    60
ttaagttttg ttttccttgg cacatkttgt rccggggtt gttagtgtgt caaccagaca   120
accatgatgc cccgtagagg caagcatgaa tgctcgtcaa caaggcctca caaggctcga   180
aacaaatgct tcggtccctg aaaggccagt agtttwtaca tgttcacggg tcgttctgct   240
atgcaggatt cgacaatgat ccttccgcag gttcacctac ggaaaccttg acgactttt   300 act                                                                 303
```

<210> SEQ ID NO 40
<211> LENGTH: 303
<212> TYPE: DNA
<213> ORGANISM: Echinacea atrorubens

<400> SEQUENCE: 40

```
ttacaaaaga agcaacgcac agtatgcaca ccaatgacgg ggcataacag cacaagccct    60
```

```
ttaagttttg ttttccttgg cacatkttgt gccgggggtt gttagtgtgt caaccagaca      120
accatgatgc cccgtagagg caagcatgaa tgctcgtcaa caaggcctca caaggctcga      180
aacaaatgct tcggtccctr aaaggccagt agtttwtaca tgttcacggg tcgttctgct      240
atgcaggatt cgacaatgat ccttccgcag gttcacctac ggaaaccttg tacgactttt      300
act                                                                   303

<210> SEQ ID NO 41
<211> LENGTH: 302
<212> TYPE: DNA
<213> ORGANISM: Echinacea angustifolia

<400> SEQUENCE: 41
ttacaaaaga agcaacgcac agtatgcaca ccaatgacgg ggcataacag cacaagccct       60
ttaagttttg ttttccttgg cacatkttgt gccgggggtt gttagtgtgt caaccagaca      120
accatgatgc cccgtagagg caagcatgaa tgctcgtcaa caaggcctca caaggctcga      180
aacaaatgct tcggtccccg aaaggccagt agtttataca tgttcacggg tcgttctgct      240
atgcaggatt cgacaatgat ccttccgcag gttyacctac ggaaaccttg tacgacttta      300
ct                                                                    302

<210> SEQ ID NO 42
<211> LENGTH: 288
<212> TYPE: DNA
<213> ORGANISM: Echinacea pallida

<400> SEQUENCE: 42
acgcacagta tgcacaccaa tracggggca taacagcaca agccctttaa gttttgtttt       60
ccttggcaca tkttgtgccg ggggttgtta gtgtgtcaac cagacaacca tgatgccccg      120
tagaggcaag catgaatgct cgtcaacaag gcctcacaag gctcgaaaca aatgcttcgg      180
tccccgaaag gccagtagtt twtacatgtt cacgggtcgt tctgctatgc aggattcgac      240
aatgatcctt ccscaggttc acctacggaa accttgtacg actttact                  288

<210> SEQ ID NO 43
<211> LENGTH: 292
<212> TYPE: DNA
<213> ORGANISM: Echinacea atrorubens

<400> SEQUENCE: 43
agcaacgcac agtatgcaca ccaatgacgg ggcataacag cacaagccct ttaagttttg       60
ttttccttgg cacatkttgt gccgggggtt gttagtgtgt caaccagaca accatgatgc      120
cccgtagagg caagcatgaa tgctcgtcaa caaggcctca caaggctcga aacaaatgct      180
tcggtcccyg aaargccagt agtttwtaca tgttcacggg tcgttctgct atgcaggatt      240
cgacaatgat ccttccgcag gttcacctac ggaaaccttg tacgacttta ct             292

<210> SEQ ID NO 44
<211> LENGTH: 295
<212> TYPE: DNA
<213> ORGANISM: Echinacea atrorubens

<400> SEQUENCE: 44
agaagcaacg cacagtatgc acaccaatga cggggcataa cagcacaagc cctttaagtt       60
ttgttttcct tggcacatkt tgtgccgggg gttgttagtg tgtcaaccag acaaccatga      120
```

| tgccccgtag aggcaagcat gaatgctcgt caacaaggcc tcacaaggct cgaaacaaat | 180 |
| gcttcggtcc cgaaaggcc agtagttttwt acatgttcac gggtcgttct gctatgcagg | 240 |
| attcgacaat gatccttccg caggttcacc tacgaaaacc ttgtacgact ttact | 295 |

<210> SEQ ID NO 45
<211> LENGTH: 298
<212> TYPE: DNA
<213> ORGANISM: Echinacea atrorubens

<400> SEQUENCE: 45

| aaaagaagca acgcacagta tgcacaccaa tgacggggca taacagcaca agccctttaa | 60 |
| gttttgtttt ccttggcaca tkttgtgccg ggggttgtta gtgtgtcaac cagacaacca | 120 |
| tgatgccccg tagaggcaag catgaatgct cgtcaacaag gcctcacaag gctcgaaaca | 180 |
| aatgcttcgg tccccgaaag gccagtagtt twtacatgtt cacgggtcgt tctgctatgc | 240 |
| aggattcgac aatgatccwt ccgcaggttc acctacggaa accttgtacg actttact | 298 |

<210> SEQ ID NO 46
<211> LENGTH: 302
<212> TYPE: DNA
<213> ORGANISM: Echinacea atrorubens

<400> SEQUENCE: 46

| ttacaaaaga agcaacgcac agtatgcaca ccaatgacgg ggcataacag cacaagccct | 60 |
| ttaagttttg ttttccttgg cacatgttgt gccgggggtt gttagtgtgt caaccagaca | 120 |
| accatgatgc cccgtagagg caagcatgaa tgctcgtcaa caaggcctca caaggctcga | 180 |
| aacaaatgct tcggtcccyg aaaggccagt agtttwtaca tgttcacggg tcgttctgct | 240 |
| atgcaggatt cgacaatgat ccttccgcag gttcacctac ggaaaccttg tacgactta | 300 |
| ct | 302 |

<210> SEQ ID NO 47
<211> LENGTH: 302
<212> TYPE: DNA
<213> ORGANISM: Echinacea paradoxa

<400> SEQUENCE: 47

| ttacaaaaga agcaacgcac agtatgcaca ccaatgacgg ggcataacag cacaagccct | 60 |
| ttaagttttg ttttccttgg cacatgttgt gccgggggtt gttagtgtgt caaccagaca | 120 |
| accatgatgc cccgtagagg caagcatgaa tgctcgtcaa caaggcctca caaggctcga | 180 |
| aacaaatgct tcggtccccg aaaggccagt agtttwtaca tgttcacggg tcgttctgct | 240 |
| atgcaggatt cgacaatgat ccttccgcag gttcacctac ggaaaccttg tacgactta | 300 |
| ct | 302 |

<210> SEQ ID NO 48
<211> LENGTH: 302
<212> TYPE: DNA
<213> ORGANISM: Echinacea atrorubens

<400> SEQUENCE: 48

| ttacaaaaga agcaacgcac agtatgcaca ccaatgacgg ggcataacag cacaagccct | 60 |
| ttaagttttg ttttccttgg cacatgttgt gccgggggtt gttagtgtgt caaccagaca | 120 |
| accatgatgc cccgtagagg caagcatgaa tgctcgtcaa caaggcctca caaggctcga | 180 |
| aacaaatgct tcggtccctr aaabgccagt agtttwtaca tgttcacggg tcgttctgct | 240 |

```
atgcaggatt cgacaatgat ccttccgcag gttcacctac ggaaaccttg tacgactttta    300
ct                                                                    302
```

<210> SEQ ID NO 49
<211> LENGTH: 301
<212> TYPE: DNA
<213> ORGANISM: Echinacea pallida

<400> SEQUENCE: 49

```
tacaaaagaa gcaacgcaca gtatgcacac caatracggg gcataacagc acaagccctt     60
taagttttgt tttccttggc acatkttgtg ccgggggttg ttagtgtgtc aaccagacaa    120
ccatgatgcc ccgtagaggc aagcatgaat gctcgtcaac aaggcctcac aaggctcgaa    180
acaaatgctt tcggtccccg aaaggccagt agtttwtaca tgttcacggg tcgttctgct    240
atgcaggatt cgacaatgat ccttccgcag gttcacctac ggaaaccttg tacgactttta    300
c                                                                     301
```

<210> SEQ ID NO 50
<211> LENGTH: 291
<212> TYPE: DNA
<213> ORGANISM: Echinacea atrorubens
<220> FEATURE:
<221> NAME/KEY: misc_feature
<222> LOCATION: (252)..(254)
<223> OTHER INFORMATION: n is a, c, g, or t

<400> SEQUENCE: 50

```
agcaacgcac agtatgcaca ccaatgacgg ggcataacag cacaagccct ttaagttttg     60
ttttccttgg cacatkttgt gccgggggtt gttagtgtgt caaccagaca accatgatgc    120
cccgtagagg caagcatgaa tgctcgtcaa caaggcctca caaggctcga aacaaatgct    180
tcggtccctg aaargccagt agtttwtaca tgttcacggg tcgttctgct atgcaggatt    240
cgacaatgat cnnnccgcag ttcacctacg gaaaccttgt acgactttac t             291
```

<210> SEQ ID NO 51
<211> LENGTH: 300
<212> TYPE: DNA
<213> ORGANISM: Echinacea atrorubens
<220> FEATURE:
<221> NAME/KEY: misc_feature
<222> LOCATION: (261)..(263)
<223> OTHER INFORMATION: n is a, c, g, or t

<400> SEQUENCE: 51

```
tacaaaagaa gcaacgcaca gtatgcrcac caatgacggg gcataacagc acaagccctt     60
taagttttgt tttccttggc acatgttgtg ccgggggttg ttagtgtgtc aaccagacaa    120
ccatgatgcc ccgtagaggc aagcatgaat gctcgtcaac aaggcctcac aaggctcgaa    180
acaaatgctt cggtcccyra aaggccagta gtttatacat gttcacgggt cgttctgcta    240
tgcaggattc gacaatgatc nnnccgcagt tcacctacgg aaaccttgta cgactttact    300
```

<210> SEQ ID NO 52
<211> LENGTH: 300
<212> TYPE: DNA
<213> ORGANISM: Echinacea atrorubens

<400> SEQUENCE: 52

```
ttacaaaaga agcaacgcac agtatgcaca ccaatgacgg ggcataacag cacaagccct     60
```

| | |
|---|---|
| ttaagttttg ttttccttgg cacatkttgt gccgggggtt gttagtgtgt caacyagaca | 120 |
| accatgatgc cccgtagagg caagcatgaa tgctcgtcaa caaggcctca caaggctcga | 180 |
| aacaaatgct tcggtccctg aaaggccagt agtttwtaca tgttcacggg tcgttctgct | 240 |
| atgcaggatt cgacaatgat ccttccgcag ttcacctacg gaaccttgta cgactttact | 300 |

<210> SEQ ID NO 53
<211> LENGTH: 299
<212> TYPE: DNA
<213> ORGANISM: Echinacea pallida
<220> FEATURE:
<221> NAME/KEY: misc_feature
<222> LOCATION: (261)..(262)
<223> OTHER INFORMATION: n is a, c, g, or t

<400> SEQUENCE: 53

| | |
|---|---|
| tacaaaagaa gcaacgcaca gtatgcacac caatracggg gcataacagc acaagccctt | 60 |
| taagttttgt tttccttggc acatkttgtg ccggggttg ttagtgtgtc aaccagacaa | 120 |
| ccatgatgcc ccgtagaggc aagcatgaat gctcgtcaac aaggcctcac aaggctcgaa | 180 |
| acaaatgctt cggtccccga aaggccagta gtttwtacat gtcacgggtc gttctgctat | 240 |
| gcaggattcg acaatgatcc nnccgcagtt cacctacgga aaccttgtac gactttact | 299 |

<210> SEQ ID NO 54
<211> LENGTH: 299
<212> TYPE: DNA
<213> ORGANISM: Echinacea atrorubens

<400> SEQUENCE: 54

| | |
|---|---|
| ttacaaaaga agcaacgcac agtatgcaca ccaatracgg ggcataacag cacaagccct | 60 |
| ttaagttttg ttttccttgg cacatkttgt gccgggggtt gttagtgtgt caaccagaca | 120 |
| accatgatgc cccgtagagg caagcatgaa tgctcgtcaa caaggcctca caaggctcga | 180 |
| aacaaatgct tcggtccccg aaaggccagt agtttwtaca tgttcacggg tcgttctgct | 240 |
| atgcaggatt cgacaatgat ckytccgcag ttcacctacg gaaaccttgt tacgactttt | 299 |

<210> SEQ ID NO 55
<211> LENGTH: 303
<212> TYPE: DNA
<213> ORGANISM: Echinacea paradoxa
<220> FEATURE:
<221> NAME/KEY: misc_feature
<222> LOCATION: (262)..(264)
<223> OTHER INFORMATION: n is a, c, g, or t

<400> SEQUENCE: 55

| | |
|---|---|
| ttacaaaaga agcaacgcac agtatgcaca ccaatgacgg ggcataacag cacaagccct | 60 |
| ttaagttttg ttttccttgg cacatkttgt rccgggggtt gttagtgtgt caaccagaca | 120 |
| accatgatgc cccgtagagg caagcatgaa tgctcgtcaa caaggcctca caaggctcga | 180 |
| aacaaatgct tcggtccccg aaaggccagt agtttwtaca tgttcacggg tcgttctgct | 240 |
| atgcaggatt cgacaatgat cnnccgcag ttcacctacg gaaaccttgt tacgactttt | 300 |
| act | 303 |

<210> SEQ ID NO 56
<211> LENGTH: 301
<212> TYPE: DNA
<213> ORGANISM: Echinacea angustifolia
<220> FEATURE:
<221> NAME/KEY: misc_feature
<222> LOCATION: (260)..(263)
<223> OTHER INFORMATION: n is a, c, g, or t

<400> SEQUENCE: 56

| | | | | | |
|---|---|---|---|---|---|
| acaaaagaag | caacgcacag | tatgcacacc | aatgacgggg | cataacagca | caagcccttt | 60 |
| aagttttgtt | ttccttggca | catgttgtgc | cgggggttgt | tagtgtgtca | accagacaac | 120 |
| catgatgccc | cgtagaggca | agcatgaatg | ctcgtcaaca | aggcctcaca | aggctcgaaa | 180 |
| caaatgcttc | ggtccctgaa | aggccagtag | tttwtacatg | ttcacgggtc | gttctgctat | 240 |
| gcaggattcg | acaatgatcn | nnncgcagtt | cacctacgga | aaccttgtta | cgactttac | 300 |
| t | | | | | | 301 |

<210> SEQ ID NO 57
<211> LENGTH: 302
<212> TYPE: DNA
<213> ORGANISM: Echinacea paradoxa

<400> SEQUENCE: 57

| | | | | | |
|---|---|---|---|---|---|
| tacaaaagaa | gcaacgcaca | gtatgcacac | caatgacggg | gcataacagc | acaagccctt | 60 |
| taagttttgt | tttccttggc | acatgttgtr | ccggggttg | ttagtgtgtc | aaccagacaa | 120 |
| ccatgatgcc | ccgtagaggc | aagcatgaat | gctcgtcaac | aaggcctcac | aaggctcgaa | 180 |
| acaaatgctt | cggtccccga | aaggccagta | gtttwtacat | gttcacgggt | cgttctgcta | 240 |
| tgcaggattc | gacaatgatc | cttccgcagt | tcacctacgg | aaaccttgtt | acgacwttta | 300 |
| ct | | | | | | 302 |

<210> SEQ ID NO 58
<211> LENGTH: 301
<212> TYPE: DNA
<213> ORGANISM: Echinacea angustifolia
<220> FEATURE:
<221> NAME/KEY: misc_feature
<222> LOCATION: (259)..(261)
<223> OTHER INFORMATION: n is a, c, g, or t

<400> SEQUENCE: 58

| | | | | | |
|---|---|---|---|---|---|
| caaaagaagc | aacgcacagt | atgcacacca | atgacgggc | ataacagcac | aagcccttta | 60 |
| agttttgttt | tccttggcac | atkttgtgcc | ggggttgtt | agtgtgtcaa | ccagacaacc | 120 |
| atgatgcccc | gtagaggcaa | gcatgaatgc | tcgtcaacaa | ggcctcacaa | ggctcgaaac | 180 |
| aaatgcttcg | gtcccygaaa | ggccagtagt | ttwtacatgt | tcacgggtcg | ttctgctatg | 240 |
| caggattcga | caatgatcnn | nccgcaggtt | cacctacgga | aaccttgta | cgactttac | 300 |
| t | | | | | | 301 |

<210> SEQ ID NO 59
<211> LENGTH: 302
<212> TYPE: DNA
<213> ORGANISM: Echinacea pallida

<400> SEQUENCE: 59

| | | | | | |
|---|---|---|---|---|---|
| acaaaagaag | caacgcacag | tatgcacacc | aatgacgggg | cataacagca | caagcccttt | 60 |
| aagttttgtt | ttccttggca | catkttgtgc | cgggggttgt | tagtgtgtca | accagacaac | 120 |
| catgatgccc | cgtagaggca | agcatgaatg | ctcgtcaaca | aggcctcaca | aggctcgaaa | 180 |
| caaatgcttc | ggtccccgaa | aggccagtag | tttwtacatg | ttcacgggtc | gttctgctat | 240 |
| gcaggattcg | acaatgatcc | ttccgcaggt | tcacctaccg | gaaaccttgt | acgacttta | 300 | ct                                                                    302

<210> SEQ ID NO 60
<211> LENGTH: 303
<212> TYPE: DNA
<213> ORGANISM: Echinacea angustifolia

<400> SEQUENCE: 60
ttacaaaaga agcaacgcac agtatgcaca ccaatgacgg ggcataacag cacaagccct      60
ttaagttttg ttttccttgg cacatkttgt gccgggggtt gttagtgtgt caaccagaca     120
accatgatgc cccgtagagg caagcatgaa tgctcgtcaa caaggcctca caaggctcga     180
aacaaatgct tcggtccccg aaaggccagt agtttwtaca tgttcacggg tcgttctgct     240
atgcaggatt cgacaatgat ccttccgcag gttcacctac ggaaaccttg ttacgacttt     300
act                                                                   303

<210> SEQ ID NO 61
<211> LENGTH: 293
<212> TYPE: DNA
<213> ORGANISM: Echinacea angustifolia
<220> FEATURE:
<221> NAME/KEY: misc_feature
<222> LOCATION: (257)..(260)
<223> OTHER INFORMATION: n is a, c, g, or t

<400> SEQUENCE: 61
aaaagaagca acgcacagta tgcacaccaa tgacggggca taacagcaca agccctttaa      60
gttttgtttt ccttggcaca tkttgtgccg ggggttgtta gtgtgtcaac cagacaacca     120
tgatgccccg tagaggcaag catgaatgct cgtcaacaag gcctcacaag gctcgaaaca     180
aatgcttcgg tccccgaaag gccagtagtt tttacatgtt crcgggtcgt tctgctatgc     240
aggattcgac aatgatnnnn ccgcaggttc acctacggaa accttgttac gac            293

<210> SEQ ID NO 62
<211> LENGTH: 299
<212> TYPE: DNA
<213> ORGANISM: Echinacea pallida

<400> SEQUENCE: 62
tacaaaagaa gcaacgcaca gtatgcacac caatracggg gcataacagc acaagccctt      60
taagttttgt tttccttggc acatkttgtg ccggggttg ttagtgtgtc aaccagacaa     120
ccatgatgcc ccgtagaggc aagcatgaat gctcgtcaac aaggcctcac aaggctcgaa     180
acaaatgctt cggtcccga aaggccagta gtttwtacat gttcacgggt cgttctgcta     240
tgcaggattc gacaatgatc cttccgcagg ttcacctacg gaaaccttgt tacgacttt      299

<210> SEQ ID NO 63
<211> LENGTH: 300
<212> TYPE: DNA
<213> ORGANISM: Echinacea angustifolia

<400> SEQUENCE: 63
caaaagaagc aacgcacagt atgcacacca atgacgggc ataacagcac aagcccttta      60
agttttgttt tccttggcac atkttgtgcc ggggttgtt agtgtgtcaa ccagacaacc     120
aagatgcccc gtagaggcaa gcatgaatgc tcgtcaacaa ggcctcacaa ggctcgaaac     180
aaatgcttcg gtcccygaaa ggccagtagt ttwtacatgt tcacgggtcg ttctgctatg     240
caggattcga caatgatcct tccgcaggtt cacctacgga aaccttgtta cgactttact     300

<210> SEQ ID NO 64
<211> LENGTH: 304
<212> TYPE: DNA
<213> ORGANISM: Echinacea angustifolia

<400> SEQUENCE: 64

```
ttacaaaaga agcaacgcac agtatgcaca ccaatgacgg ggcataacag cacaagccct     60
ttaagttttg ttttccttgg cacatkttgt gccgggggtt gttagtgtgt caaccagaca    120
accatgatgc cccgtagagg caagcatgaa tgctcgtcaa caaggcctca caaggctcga    180
aacaaatgct tcggtccccg aaaggccagt agttttwtaca tgttcacggg tcgttctgct    240
atgcaggatt cgacaatgat ccttccgcag gttcacctac ggaaaccttg ttacgacttt    300
tact                                                                 304
```

<210> SEQ ID NO 65
<211> LENGTH: 301
<212> TYPE: DNA
<213> ORGANISM: Echinacea atrorubens

<400> SEQUENCE: 65

```
caaaagaagc aacgcacagt atgcacacca atgacggggc ataacagcac aagcccttta     60
agttttgttt tccttggcac atgttgtgcc gggggttgtt agtgtgtcaa ccagacaacc    120
atgatgcccc gtagaggcaa gcatgaatgc tcgtcaacaa ggcctcacaa ggctcgaaac    180
aaatgcttcg gtccccgaaa sgccagtagt ttatacatgt tcacgggtcg ttctgctatg    240
caggattcga caatgatcct tccgcaggtt cacctacgga accttgtta cgacttttac    300
t                                                                    301
```

<210> SEQ ID NO 66
<211> LENGTH: 302
<212> TYPE: DNA
<213> ORGANISM: Echinacea angustifolia

<400> SEQUENCE: 66

```
acaaaagaag caacgcacag tatgcacacc aatgacgggg cataacagca caagcccttt     60
aagttttgtt ttccttggca catkttgtgc cgggggttgt tagtgtgtca accagacaac    120
catgatgccc cgtagaggca agcatgaatg ctcgtcaaca aggcctcaca aggctcgaaa    180
caaatgcttc ggtccccgaa aggccagtag ttttwtacatg ttcacgggtc gttctgctat    240
gcaggattcg acaatgatcc ktccgcaggt tcacctacgg aaaccttgtt acgaccttta    300
ct                                                                   302
```

<210> SEQ ID NO 67
<211> LENGTH: 302
<212> TYPE: DNA
<213> ORGANISM: Echinacea paradoxa

<400> SEQUENCE: 67

```
tcaaaagaag caacgcacag tatgcacacc aatgacgggg cataacagca caagcccttt     60
aagttttgtt ttccttggca catgttgtrc cggggttgt tagtgtgtca accagacaac    120
catgatgccc cgtagaggca agcatgaatg ctcgtcaaca aggcctcaca aggctcgaaa    180
caaatgcttc ggtccccgaa aggccagtag ttttwtacatg ttcacgggtc gttctgctat    240
gcaggattcg acaatgatcc ttccgcaggt tcacctacgg aaaccttgtt acgactttaa    300
``` ct                                                                      302

<210> SEQ ID NO 68
<211> LENGTH: 282
<212> TYPE: DNA
<213> ORGANISM: Echinacea angustifolia
<220> FEATURE:
<221> NAME/KEY: misc_feature
<222> LOCATION: (243)..(244)
<223> OTHER INFORMATION: n is a, c, g, or t

<400> SEQUENCE: 68
cagtatgcac accaatgacg gggcataaca gcacaagccc tttaagtttt gtttccttg       60 gcacatrttg tgccgggggt tgttagtgtg tcaaccagac aaccatgatg ccccgtagag      120
gcaagcatga atgctcgtca acaaggcctc acaaggctcg aaacaaatgc ttcggtcccc      180
gaaaggccag tagtttwtac atgttcacgg gtcgttctgc tatgcaggat tcgacaatga      240
tcnntccgca ggttcaccta cggaaacctt gttaccgacc tt                        282

<210> SEQ ID NO 69
<211> LENGTH: 301
<212> TYPE: DNA
<213> ORGANISM: Echinacea pallida

<400> SEQUENCE: 69
tacaaaagaa gcaacgcaca gtatgcacac caatracggg gcataacagc acaagccctt       60
taagttttgt tttccttggc acatkttgtg ccggggttg ttagtgtgtc aaccagacaa      120
ccatgatgcc ccgtagaggc aagcatgaat gctcgtcaac aaggcctcac aaggctcgaa      180
acaaatgctt cggtccccga aaggccagta gtttwtacat gtcacgggtc gttctgctat      240
gcaggattcg acaatgatcc ttccgcaggt tcacctacgg aaaccttgtt acgactttac      300
t                                                                      301

<210> SEQ ID NO 70
<211> LENGTH: 300
<212> TYPE: DNA
<213> ORGANISM: Echinacea pallida
<220> FEATURE:
<221> NAME/KEY: misc_feature
<222> LOCATION: (260)..(260)
<223> OTHER INFORMATION: n is a, c, g, or t

<400> SEQUENCE: 70 acaaagaag caacgcacag tatgcacacc aatracgggg cataacagca caagcccttt       60
aagttttgtt ttccttggca catkttgtgc cggggttgt tagtgtgtca accagacaac      120
catgatgccc cgtagaggca agcatgaatg ctcgtcaaca aggcctcaca aggctcgaaa      180
caaatgcttc ggtccccgaa aggccagtgt ttwtacatgt tcacgggtcg ttctgctatg      240
caggattcga caatgatcdn kccgcaggtt cacctacgga aaccttgtaa cgactttact     300

<210> SEQ ID NO 71
<211> LENGTH: 303
<212> TYPE: DNA
<213> ORGANISM: Echinacea angustifolia
<220> FEATURE:
<221> NAME/KEY: misc_feature
<222> LOCATION: (262)..(264)
<223> OTHER INFORMATION: n is a, c, g, or t
<220> FEATURE:
<221> NAME/KEY: misc_feature
<222> LOCATION: (277)..(279)
<223> OTHER INFORMATION: n is a, c, g, or t

<400> SEQUENCE: 71

```
tacaaaagaa gcaacgcaca gtatgcacac caatgacggg gcataacagc acaagcccTt      60
taagttttgt tttccttggc acattttgtg ccggggttg ttagtgtgtc aaccagacaa      120
ccatratgcc ccgtagaggc aagcatgaat rctcgtcaac aaggcctcac aaggctcgaa     180
aacaaatgct tcggtccccg aaargccagt agtttwtaca tgttcacggg tcgttctgct     240
atgcaggatt cgacaatgat cnnnccgcag gttcccnnng gaaaccttgt aacgactttt     300
act                                                                   303
```

<210> SEQ ID NO 72
<211> LENGTH: 303
<212> TYPE: DNA
<213> ORGANISM: Echinacea angustifolia
<220> FEATURE:
<221> NAME/KEY: misc_feature
<222> LOCATION: (260)..(261)
<223> OTHER INFORMATION: n is a, c, g, or t

<400> SEQUENCE: 72

```
caaaagaagc aacgcacagt atgcacacca atgacgggc ataacagcac aagcccttta      60
agttttgttt tccttggcac atkttgtgcc ggggttgtt agtgtgtcaa ccagacaacc      120
atgatgcccc gtagaggcaa gcatgaatgc tcgtcaacaa ggcctcacaa ggctcgaaaa    180
caaatgcttc ggtccccgaa aggccagtag tttwtacatg ttcacgggtc gttctgctat    240
gcaggattcg acaatgatcn ntccgcaggt tcacctacgg aaaccttgtw aacgactttt    300
act                                                                   303
```

<210> SEQ ID NO 73
<211> LENGTH: 300
<212> TYPE: DNA
<213> ORGANISM: Echinacea paradoxa
<220> FEATURE:
<221> NAME/KEY: misc_feature
<222> LOCATION: (261)..(264)
<223> OTHER INFORMATION: n is a, c, g, or t

<400> SEQUENCE: 73

```
tacaaaagaa gcaacgcaca gtatgcacac caatgacggg gcataacagc acaagcccTt     60
taagttttgt tttccttggc acatkttgtg ccggggttg ttagtgtgtc aaccagacaa     120
ccatgatgcc ccgtagaggc aagcatgaat gctcgtcaac aaggcctcac aaggctcgaa    180
acaaatgctt cggtccccga aaggccagta gtttwtacat gttcacgggt cgttctgcta    240
tgcaggattc gacaatgatc nnnncgcagt tcaccwbgga aacttgttac gacttttact   300
```

<210> SEQ ID NO 74
<211> LENGTH: 303
<212> TYPE: DNA
<213> ORGANISM: Echinacea paradoxa

<400> SEQUENCE: 74

```
tacaaaagaa gcaacgcaca gtatgcacac caatgacggg gcataacagc acaagcccct     60
ttaagttttg ttttccttgg cacatkttgt rccggggggtt gttagtgtgt caaccagaca   120
accatgatgc ccgtagagg caagcatgaa tgctcgtcaa caaggcctca aaggctcga     180
aacaaatgct tcggtccccg aaaggccagt agtttwtaca tgttcacggg tcgttctgct    240
atgcaggatt cgacaatgat ccttccgcag ttcacctacg gaaaccttgt acagactttta  300
```

| ctc | 303 |

<210> SEQ ID NO 75
<211> LENGTH: 305
<212> TYPE: DNA
<213> ORGANISM: Echinacea paradoxa
<220> FEATURE:
<221> NAME/KEY: misc_feature
<222> LOCATION: (261)..(264)
<223> OTHER INFORMATION: n is a, c, g, or t

<400> SEQUENCE: 75

| tacaaaagaa gcaacgcaca gtatgcacac caatgacggg gcataacagc acaagccctt | 60 |
| taagttttgt tttccttggc acatkttgtr ccggggggttg ttagtgtgtc aaccagacaa | 120 |
| ccatgatgcc ccgtagaggc aagcatgaat gctcgtcaac aaggcctcac aaggctcgaa | 180 |
| acaaatgctt cggtccccga aaggccagta gttttwtacat gttcacgggt cgttctgcta | 240 |
| tgcaggattt cgacaatgat nnnnccgcag gttcacctat cggaaacctt gttacgactt | 300 |
| ttact | 305 |

<210> SEQ ID NO 76
<211> LENGTH: 301
<212> TYPE: DNA
<213> ORGANISM: Echinacea paradoxa

<400> SEQUENCE: 76

| caaaagaagc aacgcacagt atgcacacca atgacggggc ataacagcac aagcccttta | 60 |
| agttttgttt tccttggcac atkttgtgcc ggggggttgtt agtgtgtcaa ccagacaacc | 120 |
| atgatgcccc gtagaggcaa gcatgaatgc tcgtcaacaa aggcctcaca aggctcgaaa | 180 |
| caaaatgctt cggtccccga aaggccagta gttttwtacat gttcacgggt cgttctgcta | 240 |
| tgcaggattc gacaatgatc ckyccgcagg ttcacctacg gaaaccttgt acgcttttac | 300 |
| t | 301 |

<210> SEQ ID NO 77
<211> LENGTH: 290
<212> TYPE: DNA
<213> ORGANISM: Echinacea pallida

<400> SEQUENCE: 77

| caacgcacag tatgcacacc aatracgggg cataacagca caagcccttt aagttttgtt | 60 |
| ttccttggca catkttgtgc cggggggttgt tagtgtgtca accagacaac catgatgccc | 120 |
| cgtagaggca agcatgaatg ctcgtcaaca aggcctcaca aggctcgaaa caaatgcttc | 180 |
| ggtcccgaaa ggccagtagt ttwtacatgt tcacgggtcg ttctgctatg caggmttcga | 240 |
| caatgatcct ccccgcaggt tcacctacgg aaacttgcta cgactttact | 290 |

<210> SEQ ID NO 78
<211> LENGTH: 291
<212> TYPE: DNA
<213> ORGANISM: Echinacea atrorubens

<400> SEQUENCE: 78

| cacgcacagt atgcacacca atgacggggg cataacagca caagcccttt aagttttgtt | 60 |
| ttccttggca catkttgtrc cggggggttgt tagtgtgtca accagacaac catgatgccc | 120 |
| cgtagaggca agcatgaatg ctcgtcaaca aggcctcaca aggctcgaaa caaatgcttc | 180 |
| ggtccccgaa akgccagtag tttwtacatg ttcacgggtc ggttctgcta tgcaggattc | 240 | gacaatgatc cttccgcagg ttcacctacg gaaaccttgt acgactttac t    291

<210> SEQ ID NO 79
<211> LENGTH: 298
<212> TYPE: DNA
<213> ORGANISM: Echinacea pallida

<400> SEQUENCE: 79
tacaaaagaa gcaacgcaca gtatgcaacc aatracgggg cataacagca caagcccttt    60
aagttttgtt ttccttggca catkttgtgc cggggggttgt tagtgtgtca accagacaac    120
catgatgccc cgtagaggca agcatgaatg ctcgtcaaca aggcctcaaa ggctcgaaac    180
aaatgcttcg gtccccgaaa ggccagtagt ttwtacatgt tcacgggtcg ttctgctatg    240
caggattcga caatgatcct tccgcaggtt cactacggaa accttgtacg actttact    298

<210> SEQ ID NO 80
<211> LENGTH: 303
<212> TYPE: DNA
<213> ORGANISM: Echinacea angustifolia
<220> FEATURE:
<221> NAME/KEY: misc_feature
<222> LOCATION: (261)..(263)
<223> OTHER INFORMATION: n is a, c, g, or t

<400> SEQUENCE: 80
caaaagaagc aacgcacagt atgcacacca atgacggggc ataacagcac aagcccttta    60
agttttgttt tccttggcac atkttgtgcc ggggggttgtt agtgtgtcaa ccagacaacc    120
atgatgcccc gtagaggcaa gcatgaatgc tcgtcaacaa aggcctcaca aggctcgaaa    180
caaatgcttc ggtccccgaa aggccagtag tttwtacatg ttcacggggt cgttctgcta    240
tgcaggattc gacaatgatc nnnccgcagg ttcaacctac ggaaaccttg ttacgactt    300 act    303

<210> SEQ ID NO 81
<211> LENGTH: 307
<212> TYPE: DNA
<213> ORGANISM: Echinacea angustifolia
<220> FEATURE:
<221> NAME/KEY: misc_feature
<222> LOCATION: (264)..(266)
<223> OTHER INFORMATION: n is a, c, g, or t

<400> SEQUENCE: 81
tacaaaagaa gcaacgcaca gtatgcacac caatgacggg cgcataacag cacaagccct    60
ttaagttttg ttttccttga gcacatkttg tgccggggggt tgttagtgtg tcaaccagac    120
aaccatgatg ccccgtagag gcaagcatga atgctcgtca acaaggcctc acaaggctcg    180
aaaaaaatgc ttcggtcccc gaaargccag tagtttwtac atgttcacgg gtcgttctgc    240
tatgcaggat tcgacaatag atcnnnccgc aagttcacct abggaaacct tgttaacgac    300
ttttact    307

<210> SEQ ID NO 82
<211> LENGTH: 20
<212> TYPE: DNA
<213> ORGANISM: Artificial
<220> FEATURE:
<223> OTHER INFORMATION: synthetic oligonucleotides

<400> SEQUENCE: 82
gctgcgttct tcatcgatgc                                        20

<210> SEQ ID NO 83
<211> LENGTH: 20
<212> TYPE: DNA
<213> ORGANISM: Artificial
<220> FEATURE:
<223> OTHER INFORMATION: Synthetic oligonucleotides

<400> SEQUENCE: 83
gcatcgatga agaacgcagc                                        20

<210> SEQ ID NO 84
<211> LENGTH: 18
<212> TYPE: DNA
<213> ORGANISM: Artificial
<220> FEATURE:
<223> OTHER INFORMATION: Synthetic oligonucleotides

<400> SEQUENCE: 84
acggggcgca atagcacg                                          18

<210> SEQ ID NO 85
<211> LENGTH: 20
<212> TYPE: DNA
<213> ORGANISM: Artificial
<220> FEATURE:
<223> OTHER INFORMATION: Synthetic oligonucleotides

<400> SEQUENCE: 85
cgaggccttg tcgacgtgtg                                        20

<210> SEQ ID NO 86
<211> LENGTH: 20
<212> TYPE: DNA
<213> ORGANISM: Artificial
<220> FEATURE:
<223> OTHER INFORMATION: Synthetic oligonucleotides

<400> SEQUENCE: 86
tgtatccatg atgcccctat                                        20

<210> SEQ ID NO 87
<211> LENGTH: 21
<212> TYPE: DNA
<213> ORGANISM: Artificial
<220> FEATURE:
<223> OTHER INFORMATION: Synthetic oligonucleotides

<400> SEQUENCE: 87
caagtaaaac acatgaccga g                                      21

<210> SEQ ID NO 88
<211> LENGTH: 20
<212> TYPE: DNA
<213> ORGANISM: Artificial
<220> FEATURE:
<223> OTHER INFORMATION: Synthetic oligonucleotides

<400> SEQUENCE: 88
gacggggcat aacagcacaa                                        20

<210> SEQ ID NO 89
<211> LENGTH: 20
<212> TYPE: DNA
<213> ORGANISM: Artificial

-continued

```
<220> FEATURE:
<223> OTHER INFORMATION: Synthetic oligonucleotides

<400> SEQUENCE: 89
gtgaggcctt gttgacgagc                                               20

<210> SEQ ID NO 90
<211> LENGTH: 21
<212> TYPE: DNA
<213> ORGANISM: Artificial
<220> FEATURE:
<223> OTHER INFORMATION: Synthetic oligonucleotides

<400> SEQUENCE: 90
tgttagtgtg tcaaccagac a                                             21

<210> SEQ ID NO 91
<211> LENGTH: 22
<212> TYPE: DNA
<213> ORGANISM: Artificial
<220> FEATURE:
<223> OTHER INFORMATION: Synthetic oligonucleotides

<400> SEQUENCE: 91
acatgtaaaa ctactggcct tt                                            22
```